US010981979B2

(12) United States Patent
Crowe, Jr. et al.

(10) Patent No.: US 10,981,979 B2
(45) Date of Patent: Apr. 20, 2021

(54) **HUMAN MONOCLONAL ANTIBODIES TO *STAPHYLOCOCCUS AUREUS* LUKAB TOXIN**

(71) Applicant: Vanderbilt University, Nashville, TN (US)

(72) Inventors: James E. Crowe, Jr., Nashville, TN (US); Gopal Sapparapu, Nashville, TN (US); Isaac Thomsen, Nashville, TN (US); Buddy Creech, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 16/491,271

(22) PCT Filed: Mar. 6, 2018

(86) PCT No.: PCT/US2018/021041

§ 371 (c)(1),
(2) Date: Sep. 5, 2019

(87) PCT Pub. No.: WO2018/165089

PCT Pub. Date: Sep. 13, 2018

(65) Prior Publication Data

US 2020/0010536 A1 Jan. 9, 2020

Related U.S. Application Data

(60) Provisional application No. 62/467,619, filed on Mar. 6, 2017.

(51) Int. Cl.

| | |
|---|---|
| ***C07K 16/12*** | (2006.01) |
| ***A61P 31/04*** | (2006.01) |
| ***C12N 5/16*** | (2006.01) |
| ***G01N 33/569*** | (2006.01) |
| ***G01N 33/577*** | (2006.01) |

(52) U.S. Cl.

CPC .......... *C07K 16/1271* (2013.01); *A61P 31/04* (2018.01); *C12N 5/163* (2013.01); *G01N 33/56938* (2013.01); *G01N 33/577* (2013.01); *C07K 2317/21* (2013.01); *C07K 2317/76* (2013.01); *G01N 2469/10* (2013.01); *G01N 2469/20* (2013.01); *G01N 2800/26* (2013.01)

(58) Field of Classification Search

None

See application file for complete search history.

(56) References Cited

U.S. PATENT DOCUMENTS

| | | | |
|---|---|---|---|
| 8,343,489 B2 | 1/2013 | Weaver | |
| 2011/0247693 A1* | 10/2011 | Torres | H01L 51/426 136/263 |
| 2011/0274693 A1 | 11/2011 | Torres | |
| 2014/0030269 A1 | 1/2014 | Coljee | |
| 2016/0244511 A1 | 8/2016 | Nagy et al. | |

FOREIGN PATENT DOCUMENTS

| | | |
|---|---|---|
| CN | 104098693 | 10/2014 |
| WO | WO 2004/050850 | 6/2004 |
| WO | WO 2014/187746 | 11/2014 |
| WO | WO 2015/091935 | 6/2015 |
| WO | WO 2016/197071 | 12/2016 |

OTHER PUBLICATIONS

Vajdos et al. (J Mol Biol. Jul. 5, 2002;320(2):415-28.*

Brown et al. (J Immunol. May 1996;156(9):3285-91.*

Hollevoet et al (J. Transl. Med., 15:131, 1-19, 2017).*

Badarau, Adriana, et al. "Context matters: The importance of dimerization-induced conformation of the LukGH leukocidin of *Staphylococcus aureus* for the generation of neutralizing antibodies." *MAbs*. vol. 8, No. 7, Taylor & Francis, 2016.

Chadha, Ashley D., et al. "Host response to *Staphylococcus aureus* cytotoxins in children with cystic fibrosis," *Journal of Cystic Fibrosis* 15.5 (2016): 597-604.

Daum, Robert S., and Brad Spellberg. "Progress toward a *Staphylococcus aureus* vaccine." *Clinical Infectious Diseases* 54.4 (2012): 560-567.

International Preliminary Report on Patentability issued in International Application No. PCT/US2018/021041, dated Sep. 19, 2019.

International Search Report and Written Opinion issued in International Application No. PCT/US2018/021041, dated Jun. 18, 2018.

Proctor, Richard A. "Is there a future for a *Staphylococcus aureus* vaccine?." *Vaccine* 30.19 (2012): 2921-2927.

Thomsen, Isaac P., et al. "Children with invasive *Staphylococcus aureus* disease exhibit a potently neutralizing antibody response to the cytotoxin LukAB." *Infection and Immunity* 82.3 (2014): 1234-1242.

Thomsen, Isaac P., et al. "Monoclonal antibodies against the *Staphylococcus aureus* bicomponent leukotoxin AB isolated following invasive human infection reveal diverse binding and modes of action." *The Journal of Infection Diseases* 215.7 (2017): 1124-1131.

Thomsen, Isaac, Hannah Dudney, and C. Buddy Creech. "Searching for the holy grail of a *Staphylococcal* vaccine." *Human Vaccines* 6.12 (2010): 1068-1070.

Wei et al., Machine Translation of CN 104098693 (partial), dated Oct. 15, 2014.

Yu, Xiaocong, et al. "An optimized electrofusion-based protocol for generating virus-specific human monoclonal antibodies." *Journal of immunological methods* 336.2 (2008), 142-151.

Extended European Search Report issued in European Application No. 18764566.8, dated Nov. 13, 2020.

Melehani, Jason H., et al. "Staphylococcus aureus leukocidin A/B (LukAB) kills human monocytes via host NLRP3 and ASC when extracellular, but not intracellular." *PLoS pathogens* 11.6 (2015): e1004970.

* cited by examiner

*Primary Examiner* — Brian Gangle

(74) *Attorney, Agent, or Firm* — Parker Highlander PLLC

(57) ABSTRACT

The present disclosure is directed to antibodies binding to prefusion and postfusion forms of both human *S. aureus* and human metapneumovirus F proteins, including neutralizing antibodies, and methods for use thereof.

13 Claims, 9 Drawing Sheets

Specification includes a Sequence Listing.

| | Second mAb | | |
|---|---|---|---|
| First mAb | SA-13 | SA-15 | SA-17 |
| SA-13 | -2 | 127 | 96 |
| SA-15 | 138 | -10 | 105 |
| SA-17 | 100 | 117 | 1 |

HUMAN MONOCLONAL ANTIBODIES TO *STAPHYLOCOCCUS AUREUS* LUKAB TOXIN

The application is a national phase application under 35 U.S.C. § 371 of International Application No. PCT/US2018/021041, filed Mar. 6, 2018, which claims benefit of priority to U.S. Provisional Application Ser. No. 62/467,619, filed Mar. 6, 2017, the entire contents of each of which are hereby incorporated by reference.

BACKGROUND

1. Field of the Disclosure

The present disclosure relates generally to the fields of medicine, infectious disease, and immunology. More particular, the disclosure relates to human antibodies binding to *Staphylococcus aureus.*

2. Background

Antibiotic resistance frequencies continue to rise in *Staphylococcus aureus* isolates, and there is an urgent need for improved methods to both prevent and treat *S. aureus* infections. *S. aureus* is a highly complex organism, however, and the history of failed *S. aureus* vaccine candidates dates back to at least 1902 (Wright, 1902). One major barrier to the development of novel preventive strategies is that neither the bacterial nor host factors that govern the transition of *S. aureus* from a commensal organism to a pathogen are completely understood.

*S. aureus* produces a wide array of virulence factors, but the two-component leukotoxins, in particular the newly identified cytotoxin LukAB (also known as LukGH) (Ventura et al., 2010; DuMont et al., 2011), are highly promising candidate antigens for inclusion in a multi-component vaccine. *S. aureus* secretes LukAB to disrupt the innate host response via lysis of neutrophils, macrophages, dendritic cells, and monocytes (Ventura et al., 2010; DuMont et al., 2011). Moreover, LukAB contributes to *S. aureus* fitness post-leukocyte phagocytosis (Melehani et al., 2015; DuMont et al., 2013a) and facilitates the persistence of staphylococcal biofilms (Scherr et al., 2015), both major barriers against successful use of currently available anti-staphylococcal therapeutics. LukAB induces cytolysis via pore formation that occurs following toxin binding to the CD11 b subunit of Mac-1 (DuMont et al., 2013b), an integrin found on the surface of phagocytes. Disruption of the interaction of LukAB and CD11b neutralizes cytotoxicity (DuMont et al., 2014; Badarau et al., 2015). Thus, agents that can achieve this disruption would be useful as therapeutics for *S. aureus* infection.

SUMMARY

Thus, in accordance with the present disclosure, there is provided a method of detecting a *Staphylococcus aureus* infection in a subject comprising (a) contacting a sample from said subject with an antibody or antibody fragment having heavy chain CDR1, CDR2 and CDR3 and a light chain CDR1, CDR2 and a CDR3 from Tables 3 and 4 respectively, and (b) detecting *Staphylococcus aureus* in said sample by binding of said antibody or antibody fragment to a *Staphylococcus aureus* antigen in said sample. The sample may be a body fluid, such as blood, sputum, tears, saliva, mucous or serum, urine, exudate, transudate, tissue scrapings or feces. Detection may comprise ELISA, RIA or Western blot. The method may further comprise performing steps (a) and (b) a second time and determining a change in *Staphylococcus aureus* antigen levels as compared to the first assay.

The antibody or antibody fragment may be encoded by heavy and light chain variable sequences as set forth in Table 1, by heavy and light chain variable sequences having 70%, 80%, or 90% identity to heavy and light chain variable sequences as set forth in Table 1, or by heavy and light chain variable sequences having 95% identity to heavy and light chain variable sequences as set forth in Table 1. The said antibody or antibody fragment may comprise heavy and light chain variable sequences heavy and light chain variable sequences as set forth in Table 2, heavy and light chain variable sequences having 70%, 80% or 90% identity to heavy and light chain variable sequences as set forth in Table 2, or heavy and light chain variable sequences having 95% identity to heavy and light chain variable sequences as set forth in Table 2. The antibody fragment may a recombinant scFv (single chain fragment variable) antibody, Fab fragment, $F(ab')_2$ fragment, or Fv fragment.

In another embodiment, there is provided a method of treating a subject infected with *Staphylococcus aureus*, or reducing the likelihood of infection of a subject at risk of contracting *Staphylococcus aureus*, comprising delivering to said subject an antibody or antibody fragment having heavy chain CDR1, CDR2 and CDR3 and a light chain CDR1, CDR2 and a CDR3 from Tables 3 and 4 respectively. The antibody or antibody fragment may be encoded by heavy and light chain variable sequences as set forth in Table 1, by heavy and light chain variable sequences having 70%, 80%, or 90% identity to heavy and light chain variable sequences as set forth in Table 1, or by heavy and light chain variable sequences having 95% identity to heavy and light chain variable sequences as set forth in Table 1. The said antibody or antibody fragment may comprise heavy and light chain variable sequences heavy and light chain variable sequences as set forth in Table 2, heavy and light chain variable sequences having 70%, 80% or 90% identity to heavy and light chain variable sequences as set forth in Table 2, or heavy and light chain variable sequences having 95% identity to heavy and light chain variable sequences as set forth in Table 2. The antibody fragment may a recombinant scFv (single chain fragment variable) antibody, Fab fragment, $F(ab')_2$ fragment, or Fv fragment. The antibody or antibody fragment may recognize an epitope exclusively found on LukAB, or an epitope found on LukA and LukAB and/or reduces the toxicity of LukAB, and/or inhibits LukAB-binding to the human I-domain of CD11b. The antibody or antibody fragment may be administered prior to infection, or administered after infection. Delivering may comprise antibody or antibody fragment administration, or genetic delivery with an RNA or DNA sequence or vector encoding the antibody or antibody fragment.

In yet another embodiment, there is provided a monoclonal an antibody or antibody fragment comprising heavy chain CDR1, CDR2 and CDR3 and a light chain CDR1, CDR2 and a CDR3 from Tables 3 and 4 respectively. The antibody or antibody fragment may be encoded by heavy and light chain variable sequences as set forth in Table 1, by heavy and light chain variable sequences having 70%, 80%, or 90% identity to heavy and light chain variable sequences as set forth in Table 1, or by heavy and light chain variable sequences having 95% identity to heavy and light chain variable sequences as set forth in Table 1. The said antibody or antibody fragment may comprise heavy and light chain variable sequences heavy and light chain variable sequences as set forth in Table 2, heavy and light chain variable sequences having 70%, 80% or 90% identity to heavy and light chain variable sequences as set forth in Table 2, or heavy and light chain variable sequences having 95% identity to heavy and light chain variable sequences as set forth in Table 2. The antibody fragment may a recombinant scFv (single chain fragment variable) antibody, Fab fragment, $F(ab')_2$ fragment, or Fv fragment. The antibody or antibody fragment may recognize an epitope exclusively found on LukAB, or an epitope found on LukA and LukAB and/or reduces the toxicity of LukAB, and/or inhibits LukAB-binding to the human I-domain of CD11b. The antibody or antibody fragment may further comprise a cell penetrating peptide and/or is an intrabody, or may be linked to a detectable label or therapeutic agent.

In still yet another embodiment, there is provided a hybridoma or engineered cell encoding an antibody or antibody fragment comprising heavy chain CDR1, CDR2 and CDR3 and a light chain CDR1, CDR2 and a CDR3 from Tables 3 and 4 respectively. The antibody or antibody fragment may be encoded by heavy and light chain variable sequences as set forth in Table 1, by heavy and light chain variable sequences having 70%, 80%, or 90% identity to heavy and light chain variable sequences as set forth in Table 1, or by heavy and light chain variable sequences having 95% identity to heavy and light chain variable sequences as set forth in Table 1. The said antibody or antibody fragment may comprise heavy and light chain variable sequences heavy and light chain variable sequences as set forth in Table 2, heavy and light chain variable sequences having 70%, 80% or 90% identity to heavy and light chain variable sequences as set forth in Table 2, or heavy and light chain variable sequences having 95% identity to heavy and light chain variable sequences as set forth in Table 2. The antibody fragment may a recombinant scFv (single chain fragment variable) antibody, Fab fragment, $F(ab')_2$ fragment, or Fv fragment. The antibody or antibody fragment may recognize an epitope exclusively found on LukAB, or an epitope found on LukA and LukAB and/or reduces the toxicity of LukAB, and/or inhibits LukAB-binding to the human I-domain of CD11b. The antibody or antibody fragment may further comprise a cell penetrating peptide and/or is an intrabody.

In a further embodiment, there is provided a vaccine formulation comprising one or more antibodies or antibody fragments characterized by chain CDR1, CDR2 and CDR3 and a light chain CDR1, CDR2 and a CDR3 from Tables 3 and 4 respectively. The one or more antibodies or antibody fragments may be encoded by heavy and light chain variable sequences as set forth in Table 1, by heavy and light chain variable sequences having 70%, 80%, or 90% identity to heavy and light chain variable sequences as set forth in Table 1, or by heavy and light chain variable sequences having 95% identity to heavy and light chain variable sequences as set forth in Table 1. The one or more antibodies or antibody fragments may comprise heavy and light chain variable sequences heavy and light chain variable sequences as set forth in Table 2, heavy and light chain variable sequences having 70%, 80% or 90% identity to heavy and light chain variable sequences as set forth in Table 2, or heavy and light chain variable sequences having 95% identity to heavy and light chain variable sequences as set forth in Table 2. The antibody fragment or fragments may a recombinant scFv (single chain fragment variable) antibody, Fab fragment, $F(ab')_2$ fragment, or Fv fragment. The one or more antibodies or antibody fragments may recognize an epitope exclusively found on LukAB, or an epitope found on LukA and LukAB and/or reduces the toxicity of LukAB, and/or inhibits LukAB-binding to the human I-domain of CD11b. At least one of said antibodies or antibody fragments may further comprise a cell penetrating peptide and/or is an intrabody. The vaccine formulation may comprise at least two antibodies having affinity for an epitope common to LukA and LukAB.

In an additional embodiment, there is provided a method of identifying anti-*Staphylococcus aureus*-specific monoclonal antibodies or neutralizing antibodies recognizing a LukAB-specific epitope comprising (a) contacting a candidate monoclonal antibody or polyclonal serum with LukAB in the presence of the antibody or antibody fragment characterized by chain CDR1, CDR2 and CDR3 and a light chain CDR1, CDR2 and a CDR3 from Tables 3 and 4 respectively; (b) assessing binding of said candidate monoclonal antibody or polyclonal serum to LukAB; and (c) identifying said candidate monoclonal antibody or polyclonal serum recognizing a LukAB-specific epitope when said antibody or antibody fragment blocks binding of said candidate monoclonal antibody or polyclonal serum to LukAB. The method may further comprise performing a control reaction where said candidate monoclonal antibody is contacted with LukAB and/or LukA in the absence of the antibody or antibody fragment. Detection may comprise ELISA, RIA or Western blot.

The antibody or antibody fragment may be encoded by heavy and light chain variable sequences as set forth in Table 1, by heavy and light chain variable sequences having 70%, 80%, or 90% identity to heavy and light chain variable sequences as set forth in Table 1, or by heavy and light chain variable sequences having 95% identity to heavy and light chain variable sequences as set forth in Table 1. The antibody or antibody fragment may comprise heavy and light chain variable sequences heavy and light chain variable sequences as set forth in Table 2, heavy and light chain variable sequences having 70%, 80% or 90% identity to heavy and light chain variable sequences as set forth in Table 2, or heavy and light chain variable sequences having 95% identity to heavy and light chain variable sequences as set forth in Table 2. The antibody or antibody fragment may a recombinant scFv (single chain fragment variable) antibody, Fab fragment, $F(ab')_2$ fragment, or Fv fragment.

Still another embodiment comprises a monoclonal antibody or fragment thereof, or hybridoma or engineered cell comprising the same, wherein said antibody or antibody fragment wherein said antibody or antibody fragment recognizes an epitope exclusively found on LukAB, or an epitope found on LukA and LukAB and/or reduces the toxicity of LukAB.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 2A) Primary human neutrophils from 5 donors were inoculated with WT USA300 *S. aureus* strains LAC and BK18807, and isogenic lukAB mutants, (MOI=25) for 2 h and toxicity measured in a LDH release assay (measurement of significant membrane damage/pore formation and cell lysis). Killing of PMNs in a LukAB-dependent manner is evident. (FIG. 2B) Primary human neutrophils were inoculated with WT *S. aureus* strains (a: LAC and b: BK18807) in the presence or absence of mAbs, 2.5 μg/mL, for 2 h and cell death was evaluated by measuring LDH release. Bars represent mean±SEM, with n=5 donors. *P<0.05 using one-way ANOVA with Tukey's post hoc test correction for multiple comparisons.

(FIG. 4A) LukAB binding to hPMN surface. Dilutions of mAbs were pre-incubated with a fixed concentration of Biotin-LukAB (5 μg/mL) to give indicated molar ratios. LukAB-mAb mixture was added to hPMNs (n=4 donors) on ice for 10 mins before cell washing, staining and FACS analysis. Inhibition of Biotin-LukAB binding to cell surface by SA-15 and SA-17 indicate that these antibodies are blocking the receptor binding site of the toxin. (FIG. 4B) Mab-mediated inhibition of LukAB binding to CD11b I-domain. LukAB was added to wells coated with purified human CD11b-I domain in presence or absence of mAbs and residual LukAB binding was determined. Mean±SEM are plotted. n=4 independent experiments for B, where dashed line represents LukAB binding to the I-domain in the absence of any mAb. *P<0.05 using two-way ANOVA with Tukey's post hoc test correction for multiple comparisons. Each mean was compared to IgG control for statistical analysis.

DESCRIPTION OF ILLUSTRATIVE EMBODIMENTS

Figure 1:
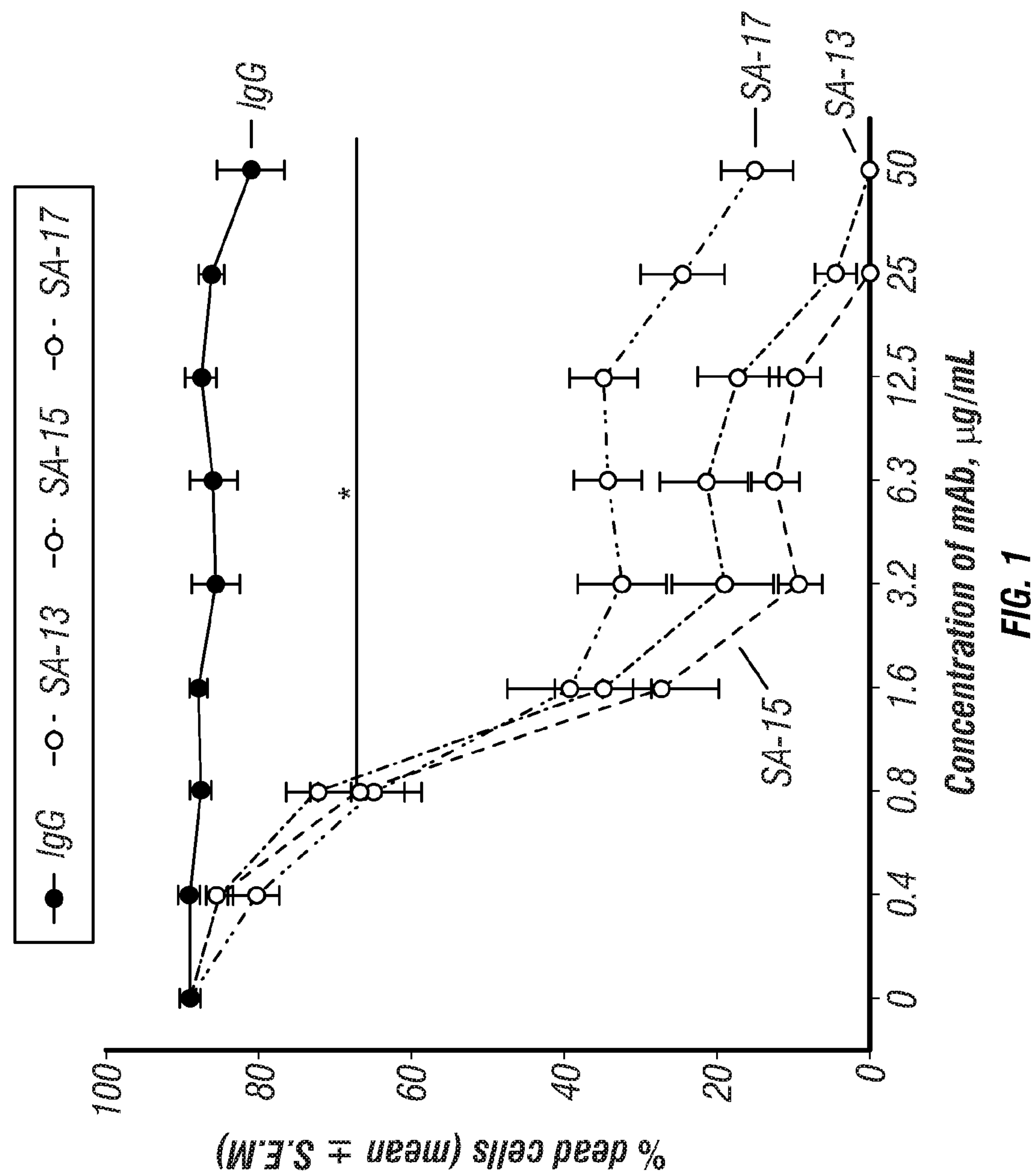
FIG. 1. SA-13, SA-15 and SA-17 neutralize LukAB-mediated cytotoxicity on primary human neutrophils. MAbs were pre-incubated with LukAB at indicated molar ratios for 30 min at room temperature. Primary human neutrophils (n=6 donors) were added to the LukAB-mAb mixture and incubated for 1 h. Neutrophil viability was evaluated with CellTiter and plotted as the mean±SEM of percentage of dead cells. *P<0.05 using two-way ANOVA with Tukey's post hoc test correction for multiple comparisons. Each mean compared to IgG control for statistical analysis.

As discussed above, antibiotic resistance frequencies continue to rise in *Staphylococcus aureus* isolates, and there is an urgent need for improved methods to both prevent and treat *S. aureus* infections. The inventor recently demonstrated that children with invasive *S. aureus* disease mount a high-titer, potently neutralizing serum antibody response to LukAB, confirming that the toxin is expressed in vivo during human infection and is targeted by the host during natural disease (Thomsen et al., 2014). Furthermore, LukAB was present in all clinical isolates tested (Thomsen et al., 2014; Chadha et al., 2016). Based on the discovery that children produce neutralizing antibodies to LukAB following infection, the inventors sought to isolate human monoclonal antibodies (mAbs) with potent neutralizing capacity following natural infection in order to study the molecular basis for recognition and toxin inhibition. They report here the isolation and characterization of a series of human mAbs against LukAB with heterologous neutralizing activity and distinct mechanisms of protection. These and other aspects of the disclosure are described in detail below.

I. *Staphylococcus aureus*

*Staphylococcus aureus* is a gram-positive, round-shaped bacterium that is a member of the Firmicutes, and is frequently found in the nose, respiratory tract, and on the skin. It is often positive for catalase and nitrate reduction and is a facultative anaerobe that can grow without the need for oxygen. Although *S. aureus* is not always pathogenic, it is a common cause of skin infections such as a skin abscess, respiratory infections such as sinusitis, and food poisoning. Pathogenic strains often promote infections by producing virulence factors such as potent protein toxins, and the expression of cell-surface proteins that bind and inactivate antibodies. The emergence of antibiotic-resistant strains of *S. aureus* such as methicillin-resistant *S. aureus* (MRSA) is a worldwide problem in clinical medicine. Despite much research and development there is no approved vaccine for *S. aureus*.

An estimated 20% of the human population are long-term carriers of *S. aureus* which can be found as part of the normal skin flora, in the nostrils, and as a normal inhabitant of the lower reproductive tract of women *S. aureus* can cause a range of illnesses, from minor skin infections, such as acne, impetigo, boils, cellulitis, folliculitis, carbuncles, scalded skin syndrome, and abscesses, to life-threatening diseases such as pneumonia, meningitis, osteomyelitis, endocarditis, toxic shock syndrome, bacteremia, and sepsis. It is still one of the five most common causes of hospital-acquired infections and is often the cause of wound infections following surgery. Each year, around 500,000 patients in hospitals of the United States contract a staphylococcal infection, chiefly by *S. aureus*.

*S. aureus* is a facultative anaerobic, gram-positive coccal (round) bacterium also known as "golden staph" and "oro staphira". *S. aureus* is non-motile and does not form spores. In medical literature, the bacterium is often referred to as *S. aureus, Staph aureus* or Staph A. *S. aureus* appears as staphylococci (grape-like clusters) when viewed through a microscope, and has large, round, golden-yellow colonies, often with hemolysis, when grown on blood agar plates. *S. aureus* reproduces asexually by binary fission. Complete separation of the daughter cells is mediated by *S. aureus* autolysin, and in its absence or targeted inhibition, the daughter cells remain attached to one another and appear as clusters.

*S. aureus* is catalase-positive (meaning it can produce the enzyme catalase). Catalase converts hydrogen peroxide ($H_2O_2$) to water and oxygen. Catalase-activity tests are sometimes used to distinguish staphylococci from enterococci and streptococci. Previously, *S. aureus* was differentiated from other staphylococci by the coagulase test. However, not all *S. aureus* strains are coagulase-positive and incorrect species identification can impact effective treatment and control measures.

A. Natural Genetic Transformation

Natural genetic transformation is a sexual process involving DNA transfer from one bacterium to another through the intervening medium, and the integration of the donor sequence into the recipient genome by homologous recombination. *S. aureus* was found to be capable of natural genetic transformation, but only at low frequency under the experimental conditions employed. Further studies suggested that the development of competence for natural genetic transformation may be substantially higher under appropriate conditions, yet to be discovered.

B. Role in Disease

While *S. aureus* usually acts as a commensal bacterium, asymptomatically colonizing about 30% of the human population, it can sometimes cause disease. In particular, *S. aureus* is one of the most common causes of bacteremia and infective endocarditis. Additionally, it can cause various skin and soft tissue infections, particularly when skin or mucosal barriers have been breached.

*S. aureus* infections can spread through contact with pus from an infected wound, skin-to-skin contact with an infected person, and contact with objects used by an infected person such as towels, sheets, clothing, or athletic equipment. Joint replacements put a person at particular risk of septic arthritis, staphylococcal endocarditis (infection of the heart valves), and pneumonia.

C. Skin Infections

Skin infections are the most common form of *S. aureus* infection. This can manifest in various ways, including small benign boils, folliculitis, impetigo, cellulitis, and more severe, invasive soft-tissue infections.

*S. aureus* is extremely prevalent in persons with atopic dermatitis. It is mostly found in fertile, active places, including the armpits, hair, and scalp. Large pimples that appear in those areas may exacerbate the infection if lacerated. This can lead to staphylococcal scalded skin syndrome, a severe form of which can be seen in neonates.

The presence of *S. aureus* in persons with atopic dermatitis is not an indication to treat with oral antibiotics, as evidence has not shown this to give benefit to the patient. The relationship between *S. aureus* and atopic dermatitis is unclear.

D. Food Poisoning

*S. aureus* is also responsible for food poisoning. It is capable of generating toxins that produce food poisoning in the human body. Its incubation period lasts one to six hours, with the illness itself lasting anywhere from thirty minutes to three days.

E. Bone and Joint Infections

*S. aureus* is the bacterium that is commonly responsible for all major bone and joint infections. This manifests in one of three forms: osteomyelitis, septic arthritis and infection from a replacement joint surgery.

F. Bacteremia

*S. aureus* is a leading cause of bloodstream infections throughout much of the industrialized world. Infection is generally associated with breakages in the skin or mucosal membranes due to surgery, injury, or use of intravascular devices such as catheters, hemodialysis machines, or injected drugs. Once the bacteria have entered the bloodstream, they can infect various organs, causing infective endocarditis, septic arthritis, and osteomyelitis. This disease is particularly prevalent and severe in the very young and very old.

Without antibiotic treatment, *S. aureus* bacteremia has a case fatality rate around 80%. With antibiotic treatment, case fatality rates range from 15% to 50% depending on the age and health of the patient, as well as the antibiotic resistance of the *S. aureus* strain.

G. Virulence Factors

Enzymes. *S. aureus* produces various enzymes such as coagulase (bound and free coagulases) which clots plasma and coats the bacterial cell, probably to prevent phagocytosis. Hyaluronidase (also known as spreading factor) breaks down hyaluronic acid and helps in spreading it. *S. aureus* also produces deoxyribonuclease, which breaks down the DNA, lipase to digest lipids, staphylokinase to dissolve fibrin and aid in spread, and beta-lactamase for drug resistance.

Toxins. Depending on the strain, *S. aureus* is capable of secreting several exotoxins, which can be categorized into three groups. Many of these toxins are associated with specific diseases.

Superantigens. Antigens known as superantigens can induce toxic shock syndrome (TSS). This group includes the toxin TSST-1, enterotoxin type B, which causes TSS associated with tampon use. This is characterized by fever, erythematous rash, hypotension, shock, multiple organ failure, and skin desquamation. Lack of antibody to TSST-1 plays a part in the pathogenesis of TSS. Other strains of *S. aureus* can produce an enterotoxin that is the causative agent of *S. aureus* gastroenteritis. This gastroenteritis is self-limiting, characterized by vomiting and diarrhea one to six hours after ingestion of the toxin, with recovery in eight to 24 hours. Symptoms include nausea, vomiting, diarrhea, and major abdominal pain.

Exfoliative toxins. Exfoliative toxins are exotoxins implicated in the disease staphylococcal scalded skin syndrome (SSSS), which occurs most commonly in infants and young children. It also may occur as epidemics in hospital nurseries. The protease activity of the exfoliative toxins causes peeling of the skin observed with SSSS.

Other Toxins. Staphylococcal toxins that act on cell membranes include alpha toxin, beta toxin, delta toxin, and several bicomponent toxins. Strains of *S. aureus* can host phages, such as the prophage Φ-PVL that produces Panton-Valentine leukocidin (PVL), to increase virulence. The bicomponent toxin PVL is associated with severe necrotizing pneumonia in children. The genes encoding the components of PVL are encoded on a bacteriophage found in community-associated MRSA strains.

Small RNA. There is a growing list of small RNAs involved in the control of bacterial virulence in *S. aureus*. For example RNAIII, SprD, RsaE, SprA1, SSR42, ArtR, SprX and Teg49.

H. Diagnosis

Depending upon the type of infection present, an appropriate specimen is obtained accordingly and sent to the laboratory for definitive identification by using biochemical or enzyme-based tests. A Gram stain is first performed to guide the way, which should show typical gram-positive bacteria, cocci, in clusters. Second, the isolate is cultured on mannitol salt agar, which is a selective medium with 7-9% NaCl that allows *S. aureus* to grow, producing yellow-colored colonies as a result of mannitol fermentation and subsequent drop in the medium's pH.

Furthermore, for differentiation on the species level, catalase (positive for all *Staphylococcus* species), coagulase (fibrin clot formation, positive for *S. aureus*), DNAse (zone of clearance on DNase agar), lipase (a yellow color and rancid odor smell), and phosphatase (a pink color) tests are all done. For staphylococcal food poisoning, phage typing can be performed to determine whether the staphylococci recovered from the food were the source of infection.

Diagnostic microbiology laboratories and reference laboratories are key for identifying outbreaks and new strains of *S. aureus*. Recent genetic advances have enabled reliable and rapid techniques for the identification and characterization of clinical isolates of *S. aureus* in real time. These tools support infection control strategies to limit bacterial spread and ensure the appropriate use of antibiotics. Quantitative PCR is increasingly being used to identify outbreaks of infection.

When observing the evolvement of *S. aureus* and its ability to adapt to each modified antibiotic, two basic methods known as "band-based" or "sequence-based" are employed. Keeping these two methods in mind, other methods such as multilocus sequence typing (MLST), pulsed-field gel electrophoresis (PFGE), bacteriophage typing, spa locus typing, and SCCmec typing are often conducted more than others. With these methods, it can be determined where strains of MRSA originated and also where they are currently.

With MLST, this technique of typing uses fragments of several housekeeping genes known as aroE, glpF, gmk, pta, tip, and yqiL. These sequences are then assigned a number which give to a string of several numbers that serve as the allelic profile. Although this is a common method, a limitation about this method is the maintenance of the microarray which detects newly allelic profiles, making it a costly and time-consuming experiment.

With PFGE, a method which is still very much used dating back to its first success in 1980s, remains capable of helping differentiate MRSA isolates. To accomplish this, the technique uses multiple gel electrophoresis, along with a voltage gradient to display clear resolutions of molecules. The *S. aureus* fragments then transition down the gel, producing specific band patters that are later compared with other isolates in hopes of identifying related strains. Limitations of the method include practical difficulties with uniform band patterns and PFGE sensitivity as a whole.

Spa locus typing is also considered a popular technique that uses a single locus zone in a polymorphic region of *S. aureus* to distinguish any form of mutations. Although this technique is often inexpensive and less time-consuming, the chance of losing discriminatory power makes it hard to differentiate between MLST CCs exemplifies a crucial limitation.

I. Treatment

The treatment of choice for *S. aureus* infection is penicillin, though nearly all human strains are now resistant to this antimicrobial agent. An antibiotic derived from some *Penicillium* fungal species, penicillin inhibits the formation of peptidoglycan cross-linkages that provide the rigidity and strength in a bacterial cell wall. The four-membered β-lactam ring of penicillin is bound to enzyme DD-transpeptidase, an enzyme that when functional, cross-links chains of peptidoglycan that form bacterial cell walls. The binding of β-lactam to DD-transpeptidase inhibits the enzyme's functionality and it can no longer catalyze the formation of the cross-links. As a result, cell wall formation and degradation are imbalanced, thus resulting in cell death. In most countries, however, penicillin resistance is extremely common, and first-line therapy is most commonly a penicillinase-resistant β-lactam antibiotic (for example, oxacillin or flucloxacillin, both of which have the same mechanism of action as penicillin). Combination therapy with gentamicin may be used to treat serious infections, such as endocarditis, but its use is controversial because of the high risk of damage to the kidneys. Honey and propolis produced by the South American bee *Tetragonisca angustula* has also been found to have antibacterial activity towards *S. aureus*. The duration of treatment depends on the site of infection and on severity.

Antibiotic resistance in *S. aureus* was uncommon when penicillin was first introduced in 1943. Indeed, the original Petri dish on which Alexander Fleming of Imperial College London observed the antibacterial activity of the *Penicillium* fungus was growing a culture of *S. aureus*. By 1950, 40% of hospital *S. aureus* isolates were penicillin-resistant; by 1960, this had risen to 80%.

MRSA is one of a number of greatly feared strains of *S. aureus* which have become resistant to most β-lactam antibiotics. For this reason, vancomycin, a glycopeptide antibiotic, is commonly used to combat MRSA. Vancomycin inhibits the synthesis of peptidoglycan, but unlike β-lactam antibiotics, glycopeptide antibiotics target and bind to amino acids in the cell wall, preventing peptidoglycan cross-linkages from forming. MRSA strains are most often found associated with institutions such as hospitals, but are becoming increasingly prevalent in community-acquired infections. A recent study by the Translational Genomics Research Institute showed that nearly half (47%) of the meat and poultry in U.S. grocery stores were contaminated with *S. aureus*, with more than half (52%) of those bacteria resistant to antibiotics. This resistance is commonly caused by the widespread use of antibiotics in the husbandry of livestock, including prevention or treatment of an infection, as well as promoting growth.

Researchers from ETH Zurich have created the endolysin Staphefekt SA.100, which is active against *S. aureus*, including MRSA.

Minor skin infections can be treated with triple antibiotic ointment.

J. Antibiotic Resistance Staphylococcal resistance to penicillin is mediated by penicillinase (a form of β-lactamase) production: an enzyme that cleaves the β-lactam ring of the penicillin molecule, rendering the antibiotic ineffective. Penicillinase-resistant β-lactam antibiotics, such as methicillin, nafcillin, oxacillin, cloxacillin, dicloxacillin, and flucloxacillin, are able to resist degradation by staphylococcal penicillinase.

Resistance to methicillin is mediated via the mec operon, part of the staphylococcal cassette chromosome mec (SCCmec). Resistance is conferred by the mecA gene, which codes for an altered penicillin-binding protein (PBP2a or PBP2') that has a lower affinity for binding β-lactams (penicillins, cephalosporins, and carbapenems). This allows for resistance to all β-lactam antibiotics, and obviates their clinical use during MRSA infections. As such, the glycopeptide vancomycin is often deployed against MRSA.

Aminoglycoside antibiotics, such as kanamycin, gentamicin, streptomycin, etc., were once effective against staphylococcal infections until strains evolved mechanisms to inhibit the aminoglycosides' action, which occurs via protonated amine and/or hydroxyl interactions with the ribosomal RNA of the bacterial 30S ribosomal subunit. Three main mechanisms of aminoglycoside resistance mechanisms are currently and widely accepted: aminoglycoside modifying enzymes, ribosomal mutations, and active efflux of the drug out of the bacteria.

Aminoglycoside-modifying enzymes inactivate the aminoglycoside by covalently attaching either a phosphate, nucleotide, or acetyl moiety to either the amine or the alcohol key functional group (or both groups) of the antibiotic. This changes the charge or sterically hinders the antibiotic, decreasing its ribosomal binding affinity. In *S. aureus*, the best-characterized aminoglycoside-modifying enzyme is aminoglycoside adenylyltransferase 4' IA (ANT (4')IA). This enzyme has been solved by X-ray crystallography. The enzyme is able to attach an adenyl moiety to the 4' hydroxyl group of many aminoglycosides, including kamamycin and gentamicin.

Glycopeptide resistance is mediated by acquisition of the vanA gene, which originates from the enterococci and codes for an enzyme that produces an alternative peptidoglycan to which vancomycin will not bind.

Today, *S. aureus* has become resistant to many commonly used antibiotics. In the UK, only 2% of all *S. aureus* isolates are sensitive to penicillin, with a similar picture in the rest of the world. The β-lactamase-resistant penicillins (methicillin, oxacillin, cloxacillin, and flucloxacillin) were developed to treat penicillin-resistant *S. aureus*, and are still used as first-line treatment. Methicillin was the first antibiotic in this class to be used (it was introduced in 1959), but, only two years later, the first case of MRSA was reported in England.

Despite this, MRSA generally remained an uncommon finding, even in hospital settings, until the 1990s, when the MRSA prevalence in hospitals exploded, and it is now endemic.

MRSA infections in both the hospital and community setting are commonly treated with non-β-lactam antibiotics, such as clindamycin (a lincosamine) and co-trimoxazole (also commonly known as trimethoprim/sulfamethoxazole). Resistance to these antibiotics has also led to the use of new, broad-spectrum anti-gram-positive antibiotics, such as linezolid, because of its availability as an oral drug. First-line treatment for serious invasive infections due to MRSA is currently glycopeptide antibiotics (vancomycin and teicoplanin). A number of problems with these antibiotics occur, such as the need for intravenous administration (no oral preparation is available), toxicity, and the need to monitor drug levels regularly by blood tests. Also, glycopeptide antibiotics do not penetrate very well into infected tissues (this is a particular concern with infections of the brain and meninges and in endocarditis). Glycopeptides must not be used to treat methicillin-sensitive *S. aureus* (MSSA), as outcomes are inferior.

Because of the high level of resistance to penicillins and because of the potential for MRSA to develop resistance to vancomycin, the U.S. Centers for Disease Control and Prevention has published guidelines for the appropriate use of vancomycin. In situations where the incidence of MRSA infections is known to be high, the attending physician may choose to use a glycopeptide antibiotic until the identity of the infecting organism is known. After the infection is confirmed to be due to a methicillin-susceptible strain of *S. aureus*, treatment can be changed to flucloxacillin or even penicillin], as appropriate.

Vancomycin-resistant *S. aureus* (VRSA) is a strain of *S. aureus* that has become resistant to the glycopeptides. The first case of vancomycin-intermediate *S. aureus* (VISA) was reported in Japan in 1996; but the first case of *S. aureus* truly resistant to glycopeptide antibiotics was only reported in 2002. Three cases of VRSA infection had been reported in the United States as of 2005.

Small non-coding RNA SprX was shown to influence *S. aureus* antibiotic resistance to Vancomycin and Teicoplanin.

K. Carriage of *S. aureus*

About one-third of the U.S. population are carriers of *S. aureus.*

The carriage of *S. aureus* is an important source of hospital-acquired infection (also called nosocomial) and community-acquired MRSA. Although *S. aureus* can be present on the skin of the host, a large proportion of its carriage is through the anterior nares of the nasal passages and can further be present in the ears. The ability of the nasal passages to harbour *S. aureus* results from a combination of a weakened or defective host immunity and the bacterium's ability to evade host innate immunity. Nasal carriage is also implicated in the occurrence of staph infections.

L. Infection Control

Spread of *S. aureus* (including MRSA) generally is through human-to-human contact, although recently some veterinarians have discovered the infection can be spread through pets, with environmental contamination thought to play a relatively unimportant part. Emphasis on basic hand washing techniques are, therefore, effective in preventing its transmission. The use of disposable aprons and gloves by staff reduces skin-to-skin contact, so further reduces the risk of transmission.

Recently, myriad cases of *S. aureus* have been reported in hospitals across America. Transmission of the pathogen is facilitated in medical settings where healthcare worker hygiene is insufficient. *S. aureus* is an incredibly hardy bacterium, as was shown in a study where it survived on polyester for just under three months; polyester is the main material used in hospital privacy curtains.

The bacteria are transported on the hands of healthcare workers, who may pick them up from a seemingly healthy patient carrying a benign or commensal strain of *S. aureus*, and then pass it on to the next patient being treated. Introduction of the bacteria into the bloodstream can lead to various complications, including endocarditis, meningitis, and, if it is widespread, sepsis.

Ethanol has proven to be an effective topical sanitizer against MRSA. Quaternary ammonium can be used in conjunction with ethanol to increase the duration of the sanitizing action. The prevention of nosocomial infections involves routine and terminal cleaning. Nonflammable alcohol vapor in CO2 NAV-CO2 systems have an advantage, as they do not attack metals or plastics used in medical environments, and do not contribute to antibacterial resistance.

An important and previously unrecognized means of community-associated MRSA colonization and transmission is during sexual contact.

*S. aureus* is killed in one minute at 78° C. and in ten minutes at 64° C.

II. Monoclonal Antibodies and Production Thereof

A. General Methods

It will be understood that monoclonal antibodies binding to human *S. aureus* will have several applications. These include the production of diagnostic kits for use in detecting and diagnosing human *S. aureus* infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

In the case of human antibodies against natural pathogens, a suitable approach is to identify subjects that have been exposed to the pathogens, such as those who have been diagnosed as having contracted the disease, or those who have been vaccinated to generate protective immunity against the pathogen. Circulating anti-pathogen antibodies can be detected, and antibody producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibody of the Present Disclosure

The antibody according to the present disclosure may be defined, in the first instance, by binding specificity. Those of skill in the art, by assessing the binding specificity/affinity of a given antibody using techniques well known to those of skill in the art, can determine whether such antibodies fall within the scope of the instant claims. In the present application, particular binding specificities are for the LukAB toxin of *S. aureus*, and the LukA subunit of *S. aureus*. At least two epitopes were identified in this study—one that is unique to the LukAB heterodimer, and one that exist both in the heterodimeric form and in the LukA monomer.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In a second aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (0 the amino acids may vary from those set out above by permitting conservative substitutions (discussed below). Each of the foregoing applies to the nucleic acid sequences set forth as Table 1 and the amino acid sequences of Table 2.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies were generated by subcloning heavy and light chain Fv DNAs from the cloning vector into an IgG plasmid vector, transfected into 293 Freestyle cells or CHO cells, and antibodies were collected an purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), $F(ab')_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency. Modifications in the Fc region can be introduced to extend the in vivo half-life of the antibody, or to alter Fc mediated functions such as complement activation, antibody dependent cellular cytotoxicity (ADCC), and FcR mediated phagocytosis.

Other types of modifications include residue modification designed to reduce oxidation, aggregation, deamidation, and immunogenicity in humans. Other changes can lead to an increase in manufacturability or yield, or reduced tissue cross-reactivity in humans.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage diplay and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

F. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. Active/Passive Immunization and Treatment/Prevention of Human *S. aureus* Infection A. Formulation and Administration The present disclosure provides pharmaceutical compositions comprising anti-human *S. aureus* antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Active vaccines are also envisioned where antibodies like those disclosed are produced in vivo in a subject at risk of human *S. aureus* infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, or by nebulizer. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

IV. Antibody Conjugates

Antibodies of the present disclosure may be linked to at least one agent to from an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. Immunodetection Methods

In still further embodiments, the present disclosure concerns immunodetection methods for binding, purifying, removing, quantifying and otherwise generally detecting Human *S. aureus* and its associated antigens. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of human *S. aureus* antibodies directed to specific viral epitopes in samples also is provided. The steps of various useful immunodetection methods have been described in the scientific literature, such as, e.g., Doolittle and Ben-Zeev (1999), Gulbis and Galand 0993), De Jager et al. (1993), and Nakamura et al. (1987). In general, the immunobinding methods include obtaining a sample suspected of containing Human *S. aureus*, and contacting the sample with a first antibody in accordance with the present disclosure, as the case may be, under conditions effective to allow the formation of immunocomplexes.

These methods include methods for purifying human *S. aureus* or related antigens from a sample. The antibody will preferably be linked to a solid support, such as in the form of a column matrix, and the sample suspected of containing the Human *S. aureus* or antigenic component will be applied to the immobilized antibody. The unwanted components will be washed from the column, leaving the human *S. aureus* antigen immunocomplexed to the immobilized antibody, which is then collected by removing the organism or antigen from the column.

The immunobinding methods also include methods for detecting and quantifying the amount of human *S. aureus* or related components in a sample and the detection and quantification of any immune complexes formed during the binding process. Here, one would obtain a sample suspected of containing human *S. aureus* or its antigens, and contact the sample with an antibody that binds human *S. aureus* or components thereof, followed by detecting and quantifying the amount of immune complexes formed under the specific conditions. In terms of antigen detection, the biological sample analyzed may be any sample that is suspected of containing human *S. aureus* or Human *S. aureus* antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to human *S. aureus* or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected. In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the human *S. aureus* or human *S. aureus* antigen is added to the wells. After binding and washing to remove non-specifically bound immune complexes, the bound antigen may be detected. Detection may be achieved by the addition of another anti-human *S. aureus* antibody that is linked to a detectable label. This type of ELISA is a simple "sandwich ELISA." Detection may also be achieved by the addition of a second anti-Human *S. aureus* antibody, followed by the addition of a third antibody that has binding affinity for the second antibody, with the third antibody being linked to a detectable label.

In another exemplary ELISA, the samples suspected of containing the human *S. aureus* or human *S. aureus* antigen are immobilized onto the well surface and then contacted with the anti-human *S. aureus* antibodies of the disclosure. After binding and washing to remove non-specifically bound immune complexes, the bound anti-human *S. aureus* antibodies are detected. Where the initial anti-human *S. aureus* antibodies are linked to a detectable label, the immune complexes may be detected directly. Again, the immune complexes may be detected using a second antibody that has binding affinity for the first anti-human *S. aureus* antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-β-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of human *S. aureus* antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventors propose the use of labeled human *S. aureus* monoclonal antibodies to determine the amount of human *S. aureus* antibodies in a sample. The basic format would include contacting a known amount of human *S. aureus* monoclonal antibody (linked to a detectable label) with human *S. aureus* antigen or particle. The human *S. aureus* antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, the present disclosure concerns immunodetection kits for use with the immunodetection methods described above. As the antibodies may be used to detect human *S. aureus* or human *S. aureus* antigens, the antibodies may be included in the kit. The immunodetection kits will thus comprise, in suitable container means, a first antibody that binds to human *S. aureus* or human *S. aureus* antigen, and optionally an immunodetection reagent.

In certain embodiments, the human *S. aureus* antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the human *S. aureus* or human *S. aureus* antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

VI. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Donor Subject. A 12 year-old boy was admitted to the Monroe Carell Jr. Children's Hospital at Vanderbilt and was enrolled into this study after confirmation of invasive *S. aureus* disease (osteomyelitis with associated bacteremia) and following written informed consent (parent) and assent. Peripheral blood was collected upon enrollment and eight weeks post-recovery in heparin tubes for isolation of PBMC and in serum separator tubes.

Generation of LukAB-reactive mAbs. Hybridomas producing antibodies against LukAB were generated as described before (Yu et al., 2008) and detailed in Supplementary Methods. Briefly, B cells isolated from a patient with invasive *S. aureus* disease were transformed with Epstein Barr virus and screened for specific antibody production. Cells with desired reactivity were electrofused with HMMA2.5 myeloma partner and grown in culture medium supplemented with HAT and ouabain for generating stable hybridomas. Hybridomas were cultured in serum free medium (Hybridoma SFM, Life Technologies) for antibody expression. Antibodies were purified from culture supernatants by affinity chromatography using HiTrap MabSelect SuRe columns (Life Technologies). The sequence of the variable portions of heavy and light chains were determined as described before and detailed in Supplementary Methods.

ELISA and epitope binning assays. Binding of purified antibodies to LukA, LukB or LukAB was detected in ELISA. The antigens were immobilized (62.5 μg/well) on microtiter plates. Antibodies diluted in PBS at various concentrations were applied and the bound antibodies were detected using anti-human IgG antibodies conjugated to peroxidase. The data were plotted using Prism (GraphPad), and non-linear regression analysis was performed to calculate the half-maximal binding concentrations ($EC_{50}$).

Competition binding studies using biolayer interferometry were performed on an Octet RED biosensor (Pall ForteBio) as described before (Flyak et al., 2015). LukAB was immobilized onto an anti-His tag antibody coated biosensor tips by immersing in protein solution at 15 μg/mL for 2 min. After a brief washing step, biosensor tips were immersed first into the wells containing first antibody at a concentration of 10 μg/mL and then into the wells containing a second mAb at a concentration of 10 μg/mL. The percent binding of the second mAb in the presence of first mAb was determined by comparing the maximal signal of the second mAb applied after the first mAb complex to the maximal signal of the second mAb alone.

Neutralization of toxin-induced PMN cytotoxicity by mAbs. Primary human neutrophils (PMNs) were isolated from blood samples as previously described (Reyes-Robles et al., 2016), and PMN purity was 90-95% as determined by flow cytometric analysis using an LSR-II flow cytometer (BD Biosciences). Serial dilutions of each mAb were mixed with a fixed amount of purified LukAB (90% lethal dose, $LD_{90}$=0.6 μg/mL) to give indicated molar ratios. Samples were pre-incubated for 30 min at room temperature before adding $2\times10^5$ PMNs in a final reaction volume of 100 μL. Cells were incubated for 1 h at 37° C. and 5% CO2 before addition of CellTiter as described previously (Thomsen et al., 2014). For experiments evaluating the cooperative effects of mAb-mediated toxin neutralization, the inventors used mixtures of mAbs at a final concentration of 3.2 μg/mL (2:1 mAb:LukAB molar ratio).

Ex vivo infection of PMNs. Overnight cultures of WT *S. aureus* strains of USA300 lineage BK18807 (Melehani et al., 2015), LAC (DuMont et al., 2011; Diep et al., 2006), and their isogenic lukAB mutant strains grown in RPMI (Invitrogen) supplemented with 1% Casamino Acids (RPMI+CAS), were sub-cultured 1:100 in RPMI+CAS and incubated for 5 h with shaking at 180 rpm. Cell pellets were washed and normalized to equal density prior to infection. Normalized *S. aureus* cultures were used to infect primary PMNs, seeded at $2\times10^5$ cells/well, at a multiplicity of infection (MOI) of 25 in a final volume of 100 μL for 2 h at 37° C. and 5% CO2. Where indicated, mAbs were added to the infection at 2.5 μg/mL immediately prior to starting the 2 h incubation. The LDH release assay was performed as previously described (Melehani et al., 2014), using the CytoTox-ONE homogeneous membrane integrity assay (Promega).

Mab-mediated inhibition of LukAB binding to cells. Biotinylated LukAB proteins used in the binding experiments were generated using the Sulfo-NHS-LC-biotin (Thermo Scientific). Biotin-LukAB was incubated with PMNs for 10 min on ice. Post-intoxication, cells were washed with PBS, stained with a PerCP-Cy5.5 Streptavidin (Biolegend), washed with FACS buffer (1×PBS+2% FBS+0.05% sodium azide) before being fixed (1×PBS+2% paraformaldehyde+2% FBS+0.05% sodium azide), and fluorescence analyzed using an LSR-II flow cytometer. For experiments including mAbs, dilutions of antibodies were pre-incubated with a fixed concentration of Biotin-LukAB (5 μg/mL) to give indicated molar ratios. Samples were incubated for 30 min at RT before adding hPMNs ($2\times10^5$ cells/well), followed by 10 min ice incubation and processed for FACS analysis as described above.

The inventors evaluated mAb-mediated inhibition of LukAB binding to I domain of CD11b by ELISA. Plates were coated with I-domain and blocked as described (Ueda et al., 1994). LukAB (0.5 μg/mL) was pre-incubated with each mAb at the indicated molar ratio in 100 pt of Blotto buffer for 30 min before being added to the wells for 30 min. Bound LukAB was detected with 100 μL of anti-LukA rabbit polyclonal Ab (Melehani et al., 2014) at a 1:2,000 dilution for 1 h and then 100 μL of HRP conjugated anti-rabbit IgG (Promega) at a 1:3,000 dilution for 1 h. Wells were incubated with 100 μL of 1-Step Ultra TMB-ELISA substrate solution (Thermo Scientific) followed by 100 μL of 1 N $H_2SO_4$. Color development was measured at 450 nm on a spectrophotometer.

Murine model of disseminated *S. aureus* infection. For the murine disseminated infection model, an erythromycin-sensitive derivative of the USA300 strain LAC was used (Boles et al., 2010). To prepare inocula, overnight cultures were back-diluted 1:100 in fresh Tryptic Soy Broth (TSB) and grown for 3 h at 37° C. with 180 rpm shaking. Bacteria then were harvested by centrifugation and suspended in PBS at a final density of approximately $2.5\times10^8$ colony forming units (CFU)/mL.

7-8 week female BALB/cJ mice were subjected to disseminated *S. aureus* infection by retro-orbital inoculation (Hammer et al., 2014; Kehl-Fie et al., 2013). Mice were pretreated with a 1:1 mixture of mAbs SA-15 and SA-17 or an isotype control (PERT-142) via intraperitoneal injection 20 h prior to inoculation. Bacterial inocula were prepared as above and then administered as a 100 μL retro-orbital injection containing approximately $2.5\times10^7$ CFU. Mice were monitored for 96 hours, after which time they were euthanized and the hearts, kidneys, and livers were removed for bacterial enumeration. Organs were homogenized using a Bullet Blender Storm (Next Advance, Averill Park, N.Y.) and Navy Lysis Tubes, then serially diluted onto TSA plates for CFU enumeration.

Statistical Analysis. Differences in cell viability for in vitro and ex vivo cytotoxicity assays and mAb-mediated inhibition of LukAB binding were analyzed using analysis of variance (ANOVA), with Tukey's post hoc test correction for multiple comparisons to determine specific differences. For the murine infection model, differences in CFU burdens in each organ were analyzed by Wilcoxon rank-sum test, assuming nonparametric distribution. Statistical analyses were performed using Prism 6.0 (GraphPad, La Jolla, Calif.).

Generation of hybridomas. B cells were transformed by infection with Epstein Barr virus (EBV) obtained from the supernatant of cultured B95.8 cotton top tamarin lymphoblastoid line (obtained previously from American Type Culture Collection (ATCC); item has been discontinued by ATCC). The transformation medium also included 2.5 μg/mL TLR agonist CpG (phosphorothioate-modified oligodeoxynucleotide ZOEZOEZZZZZOEEZOEZZZT (SEQ ID NO: 41), Life Technologies), 10 μM Chk2 inhibitor (Chk2i, Sigma), 10 μg/mL cyclosporine A (Sigma), and the mix was plated in 384-well culture plates. After 7 days of culture, cells from one 384-well culture plate were expanded into four 96-well culture plates containing CpG, Chk2i and irradiated heterologous human PBMCs to serve as feeder layers for the growth of lymphoblastoid cell line (LCL) clusters. After an additional 3 days of culture, the supernatants were screened for binding to recombinant LukAB protein by ELISA. A 5 μL volume of supernatant from each well of transformed B cell cultures (in a total assay volume of 50 μL were added to the wells coated with 2.5 μg/mL LukAB protein. The bound antibodies were detected using alkaline phosphatase conjugated goat anti-human Ig (γ and αchain specific) (Southern Biotech). In toxin neutralization screening assays, 10 μL of supernatants were mixed with 10 μL of LukAB toxin and the complexes were added to neutrophil cultures, as described below. Supernatants from LCL cultures (diluted 1:10 in assay buffer) that had been selected in separate experiments for reactivity to unrelated targets were used as negative controls.

Cells from wells with desired activity were subjected to electrofusion with HMMA2.5 myeloma cells. The fused cells then were cultured in a selective medium containing 100 μM hypoxanthine, 0.4 μM aminopterin, 16 μM thymidine (HAT Media Supplement, Sigma HO262), and 7 μg/mL ouabain (Sigma 03125) and incubated for 14-18 days before screening hybridomas for antibody production by ELISA. Cells from the positive wells were cloned biologically by sorting single cells into 384-well plates using a FACSAria III fluorescence-activated cell sorter (Becton Dickinson), cultured for about 14 days and screened for specific antibody production.

Sequence analysis of antibody variable region genes. Total RNA was extracted from hybridoma cells and used for amplification of genes coding for the variable domains of the antibody clones. First-strand cDNA synthesis and RT-PCR were done with gene-specific primers (Thornburg et al., 2016) using the OneStep RT-PCR kit (Qiagen), according to the manufacturer's protocols. The thermal cycling parameters were as follows: 50° C. for 30 min, 95° C. for 15 min, 39 cycles of (94° C. for 1 min, 55° C. for 1 min and 72° C. for 1 min) followed by a final extension step for 10 min at 72° C. PCR products were purified using Agencourt AMPure XP magnetic beads (Beckman Coulter) and sequenced directly using an ABI3700 automated DNA sequencer without cloning. Heavy chain or light chain antibody variable region sequences were analyzed using the IMGT/V-Quest program (Brochet et al., 2008). The analysis involved the identification of germline genes that were used for antibody production, location of complementary determining regions (CDRs) and framework regions (FRs) as well as the number and location of somatic mutations that occurred during affinity maturation.

Expression and purification of antibodies. For expression of antibodies from hybridoma clones, cells were cultured in serum-free medium, Hybridoma SFM (Life Technologies), for 21 days. Antibodies were harvested from the supernatants by affinity chromatography on HiTrap MabSelect SuRe columns (Life Technologies) according to the manufacturer's instructions Antibodies eluted from affinity columns were concentrated using Amicon centrifugal filters (Millipore). The inventors used similarly prepared human IgG mAbs, directed to pertussis toxin (designated PERT-142 and PERT-204) or to an unrelated *S. aureus* surface protein, IsdA (designated SA-22) as a control reagent in many of the experiments.

Isolation of primary human polymorphonuclear leukocytes (PMNs). PMNs were isolated from blood samples, as previously described (Reyes-Robles et al., 2016). Briefly, red blood cells were diminished through separation by 3% dextran (Dextran 500; Pharmacosmos) solution in endotoxin-free 0.9% sodium chloride (Baxter), and the remaining white blood cells were separated by Ficoll density centrifugation (Ficoll-Paque PLUS; GE). PMNs were isolated and suspended in Roswell Park Memorial Institute (RPMI without phenol red; Gibco) medium supplemented with 10% heat-inactivated fetal bovine serum (FBS, Gemini Bio-Products). PMN purity was 90-95% as determined by flow cytometric analysis using an LSR-II flow cytometer (BD Biosciences).

Toxin neutralization assays on human immune cells. Human promyelocytic HL-60 cells (ATCC) were cultured in RPMI 1640 (Cellgro) supplemented with 10% heat inactivated fetal bovine serum (FBS), 100 μg/mL Penicillin and 100 μg/mL Streptomycin (Pen/Strep, Cellgro), and allowed to differentiate to polymorphonuclear-like cells (PMN-HL60) for 3 days with 1.5% DMSO per standard techniques (Dumont et al., 2011). Human Acute Monocytic Leukemia THP-1 cells (ATCC) were cultured in RPMI 1640+L-Glutamine (Gibco) with 10% HI FBS (Gibco) and 1% Streptomycin (Pen/Strep, Gibco), and allowed to differentiate to macrophages with 10 nM PMA (Sigma) for 72 h at 37° C., 5% CO2 per standard techniques (Park et al., 2007). To measure the neutralization capacity of individual mAbs, serial dilutions of each mAb were mixed with a fixed amount of purified LukAB (1.25 μg/ml) to give indicated molar ratios. Samples, in triplicate wells of a 96-well microtiter plate, were incubated for 30 min at RT. Toxin-only wells served as positive toxicity controls, while media only wells served as un-intoxicated control. Differentiated HL-60 cells (PMN-HL60) or THP-1 cells were added ($1\times10^5$ cells/well) to the LukAB-mAb complexes and incubated at 37° C.+5% CO2 for one hour. The final reaction volume was 100 μL. To measure cell viability and metabolism, CellTiter (10 μL/well) (Promega) was added to the wells and incubated for 2 h. Color development was read at 490 nm using a spectrophotometer.

Example 2—Results

Isolation of LukAB-reactive human IgG mAbs. The inventors sought to isolate toxin-neutralizing mAbs reactive with LukAB from a subject with recent invasive *S. aureus* infection. PBMCs were isolated from a 12 year-old boy with confirmed *S. aureus* bacteremia and multifocal osteomyelitis. Cultures from the blood and debrided bone confirmed MRSA (PVL-positive, USA300 lineage).

Serum from the subject possessed a high titer of antibodies binding LukAB protein by ELISA (1:10,240). The inventors obtained blood from this patient in the acute phase and 2 months after recovery. B cells in the PBMC sample were transformed with EBV, and the LCL supernatants were screened for binding to LukAB and separately for neutralization of LukAB-mediated cytotoxicity. Four or 9 wells of the 384 wells tested were positive for LukAB binding, from acute or convalescent samples, respectively. The wells contained, on average, approximately 30 transformed lymphoblastoid cell clones, based on cell cluster count. Therefore, the estimated circulating memory B cell frequency of LukAB-reactive clones in the donor was 0.03% or 0.08% for acute or convalescent samples, respectively. Three of the cell line supernatants exhibited potent neutralization of LukAB-mediated cytotoxicity. B cells from wells exhibiting IgG binding to LukAB were used to generate hybridoma cell lines. The inventors obtained a panel of three distinct IgG clones with LukAB-neutralizing activity, designated SA-13 (from the acute sample), and SA-15 and SA-17 (from the convalescent sample). Each of the antibodies was encoded by different antibody variable genes, indicating that the clones arose independently (Table S1).

Figure 7A:
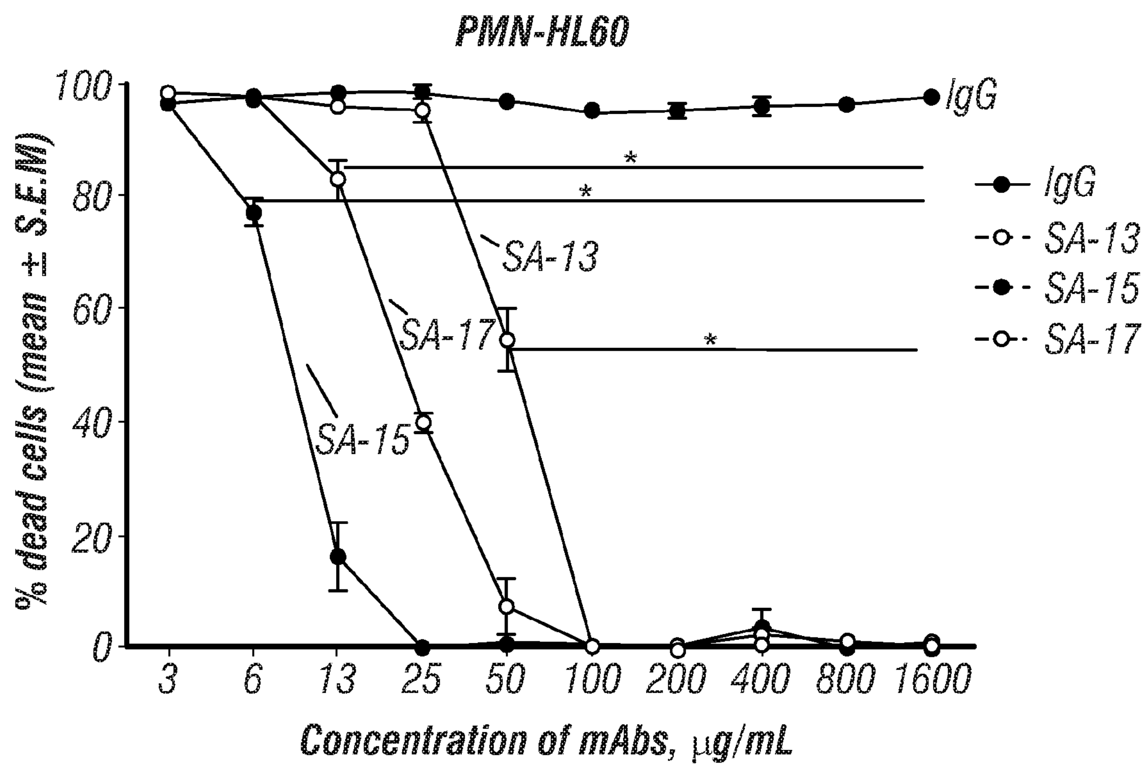
FIGS. 7A-B. Protective effect of SA-13, SA-15, SA-17 on PMN-HL60 or THP1 cell lines.
Figure 7B:
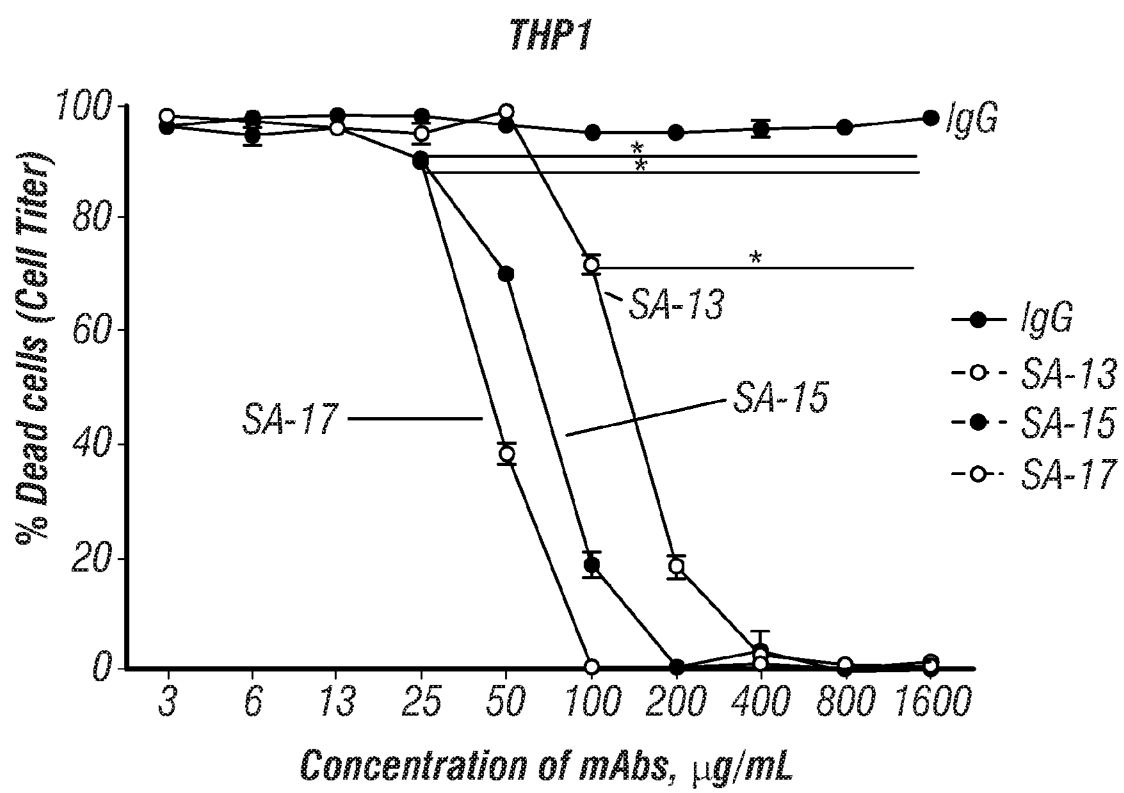
Figure 8:
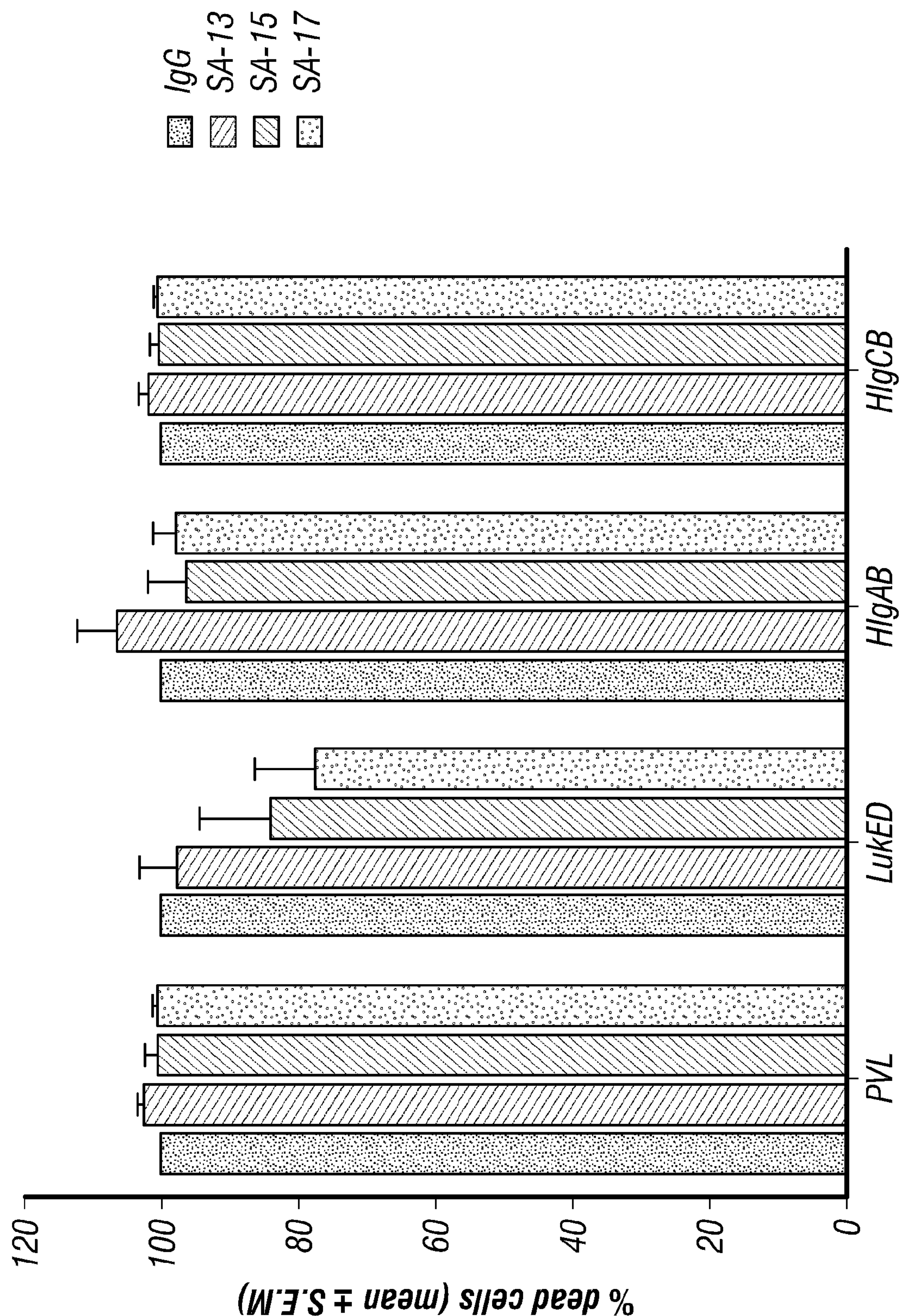
FIG. 8. Cross-reactive capacity of mAbs against other bicomponent leukocidins. MAbs at a 25 μg/mL concentration were pre-incubated with one of the indicated leukocidins (calculated $LD_{90}$: PVL—0.6 μg/mL; LukED/HlgAB—2.5 μg/mL; HlgCB—1.25 μg/mL) for 30 min at room temperature. Primary human neutrophils were added to the toxin/antibody mixture and incubated for 1 hr. Neutrophil viability was evaluated with CellTiter. Bars represent mean±SEM, with n=6 donors.

Neutralizing potency of mAbs in diverse types of PMN culture. Purified IgG preparations of the mAbs were tested for their ability to inhibit LukAB-mediated cytotoxicity in PMN cultures. Each of the three mAbs exhibited strong neutralization of cytotoxicity against primary human PMNs, with SA-15 and SA-13 exhibiting higher potency compared to SA-17, while the IgG control did not affect LukAB cytotoxicity (FIG. 1). These results suggest that the mAbs may mediate inhibition by recognizing distinct epitopes on LukAB or with differing affinity. Antibody potency also varied by cell type employed in the neutralization assays. SA-15 was significantly more potent in the protection of PMN-like HL-60 cells (FIG. 7A). In contrast, SA-17 exhibited greater potency in the protection of macrophage-like THP-1 cells (FIG. 7B). Taken together, these studies showed that the three mAbs inhibit the cytotoxic effect of purified LukAB against phagocytes.

Figures 2A, 2B:
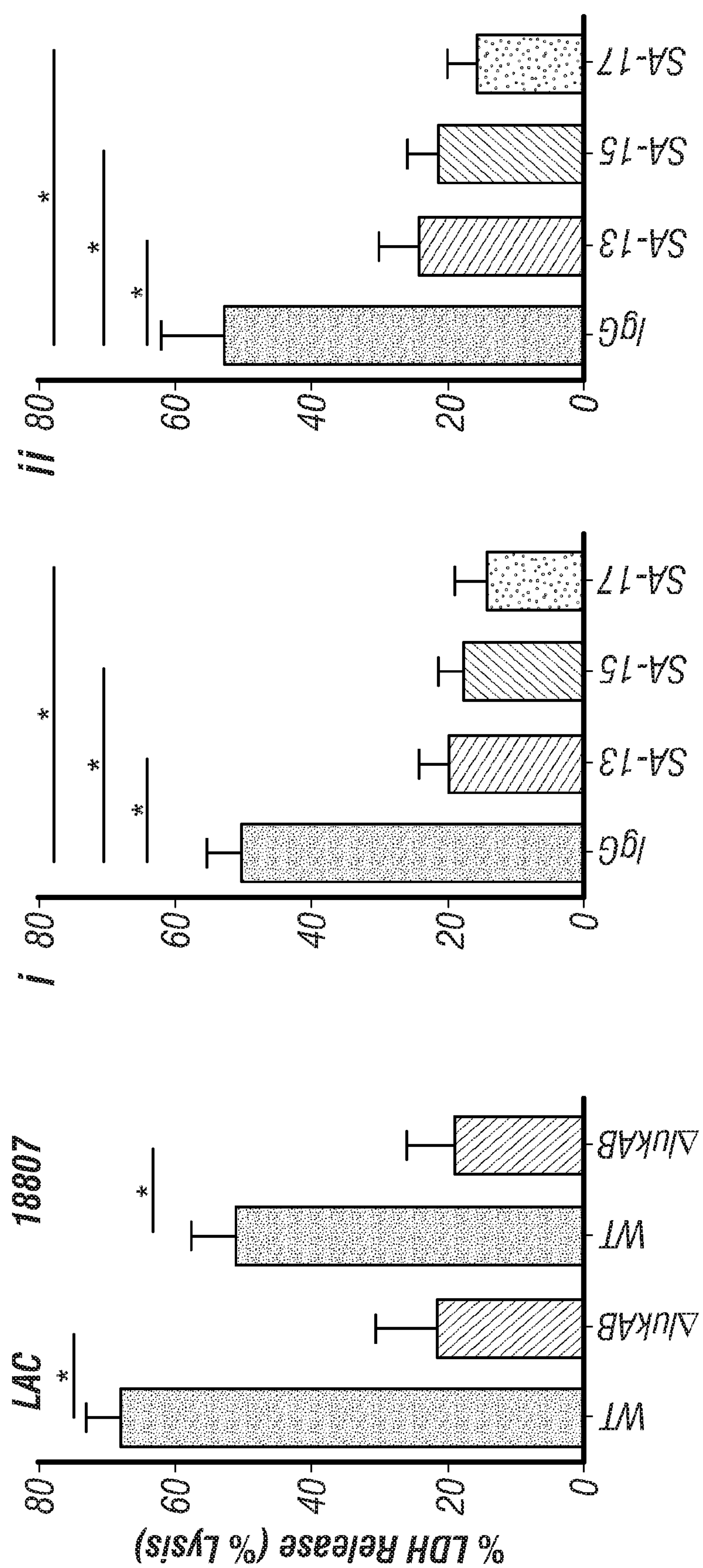
FIGS. 2A-B. SA-13, SA-15 and SA-17 neutralize cytotoxicity caused by *S. aureus* USA300 strains during ex vivo infection of primary human neutrophils.

Neutralization of *S. aureus*-mediated cytotoxicity during ex vivo infection of PMNs. Next, the inventors sought to determine if the mAbs could prevent cytotoxic effects mediated by *S. aureus* by employing an ex vivo model of infection, where primary human PMNs were infected with *S. aureus* strains of the USA300 lineage. For comparison, they also tested the cytotoxic effect of isogenic strains where LukAB was deleted. Each of the LukAB-reactive mAbs protected the PMNs against cytotoxic effects of wild-type *S. aureus* to a degree equivalent to strains in which lukAB was deleted (FIGS. 2A-B). Similar to the findings from in vitro assays, the mAbs neutralized cytotoxicity with different potency, with SA-17 showing the highest degree of cellular protection.

Figure 3A:
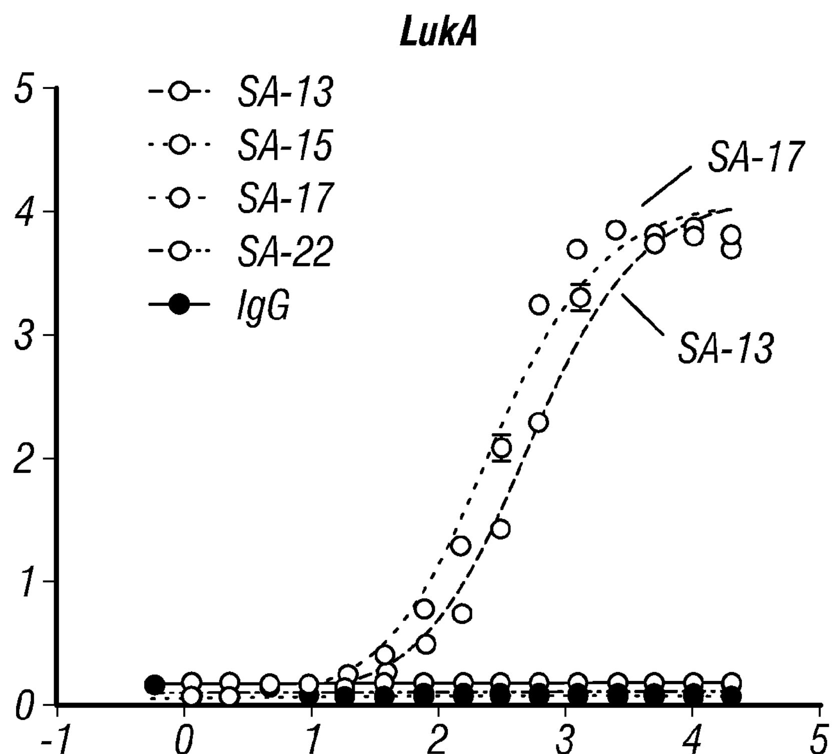
FIGS. 3A-D. Diverse patterns of recognition. The three anti-LukAB antibodies (SA-13, SA-15, and SA-17) and two irrelevant controls (SA-22 and IgG) were tested for binding to immobilized LukA, LukB monomers or LukAB heterodimer (FIG. 3A, 3B, or 3C, respectively). SA-13 and SA-17 bound both the LukA monomer and the LukAB heterodimer, while SA-15 bound only the heterodimer, suggesting that SA-15 binds to a conformational epitope present only after dimerization. None of the antibodies exhibited reduced binding in the presence of a competing antibody, suggesting unique epitopes for each of the three antibodies (FIG. 3D).
Figure 3B:
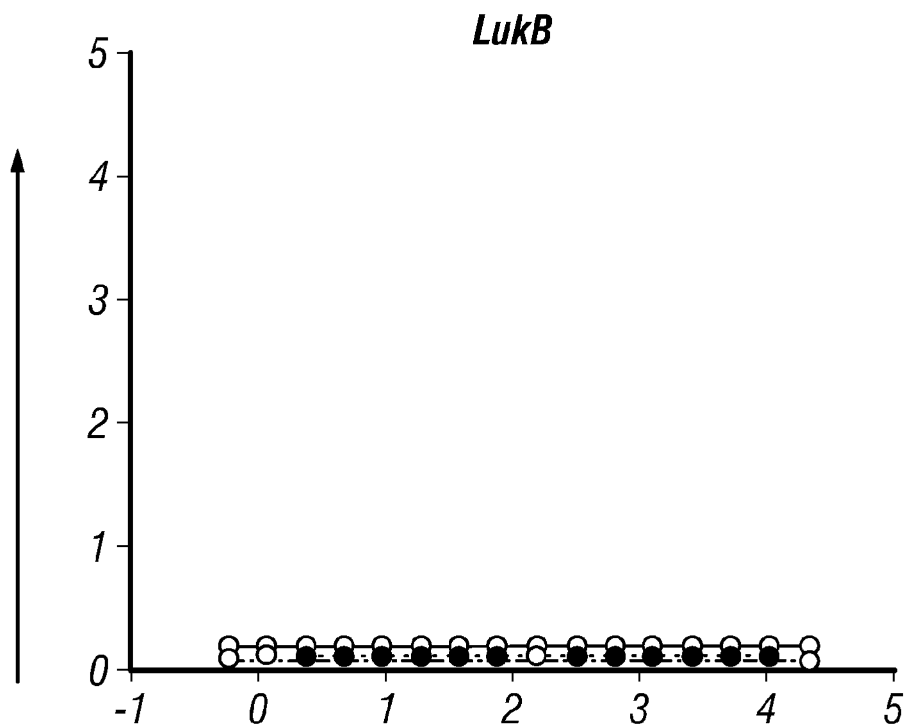
Figures 3C, 3D:
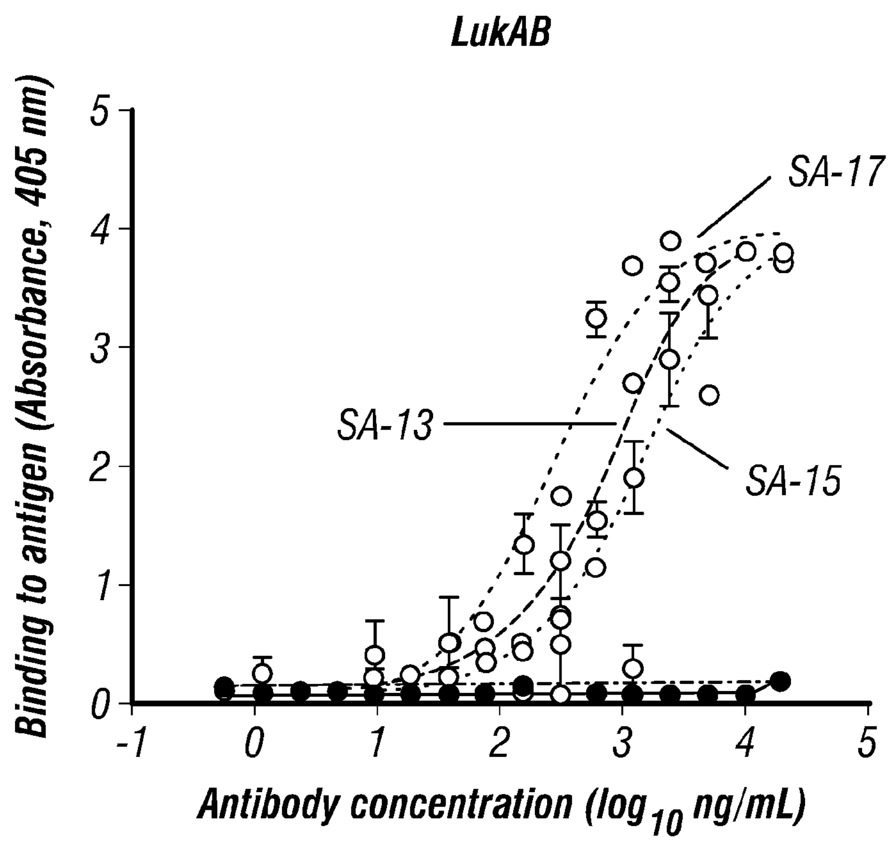

Diverse patterns of recognition of LukAB. The inventors next sought to determine the molecular basis for variation in potency seen among human mAbs targeting LukAB by defining the epitopes recognized by the mAbs. LukAB is composed of two separate monomers, LukA and LukB, but is isolated as a dimer in solution (DuMont et al., 2014; Badarau et al., 2015). To assess the region where each mAb binds, the inventors tested the ability of each anti-LukAB mAb to bind to LukA or LukB monomers and to the heterodimeric toxin. As evident in initial screens, all mAbs bound to the LukAB dimer (FIGS. 3A-D). Two of the mAbs, SA-13 and SA-17, also bound to monomeric LukA protein, but not to monomeric LukB (FIGS. 3 A-C). These results suggest a binding site on the LukA monomer that remains available after toxin dimerization. In contrast, mAb SA-15 bound exclusively to the dimeric toxin, suggesting a binding site that does not form or become accessible until after toxin dimerization. These findings demonstrate that human B cells recognize sites on both the LukA monomer and the dimerized form of LukAB during natural infection. The diverse pattern of epitope recognition of these antibodies also was evident when tested using competition-binding studies with LukAB immobilized on biosensors (FIG. 3D). The lack of competition for any combination of the mAbs demonstrates that the three mAbs described herein recognize distinct epitopes.

Figure 4B:
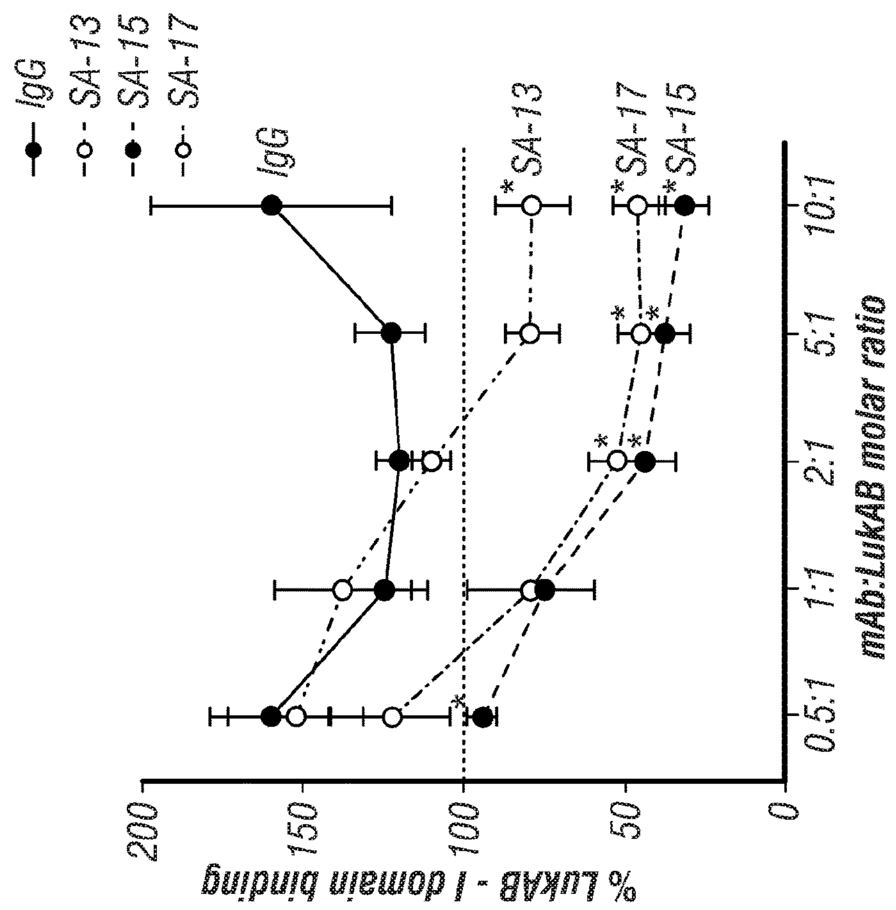
FIGS. 4A-B. MAb-mediated inhibition of LukAB binding.
Figure 4A:
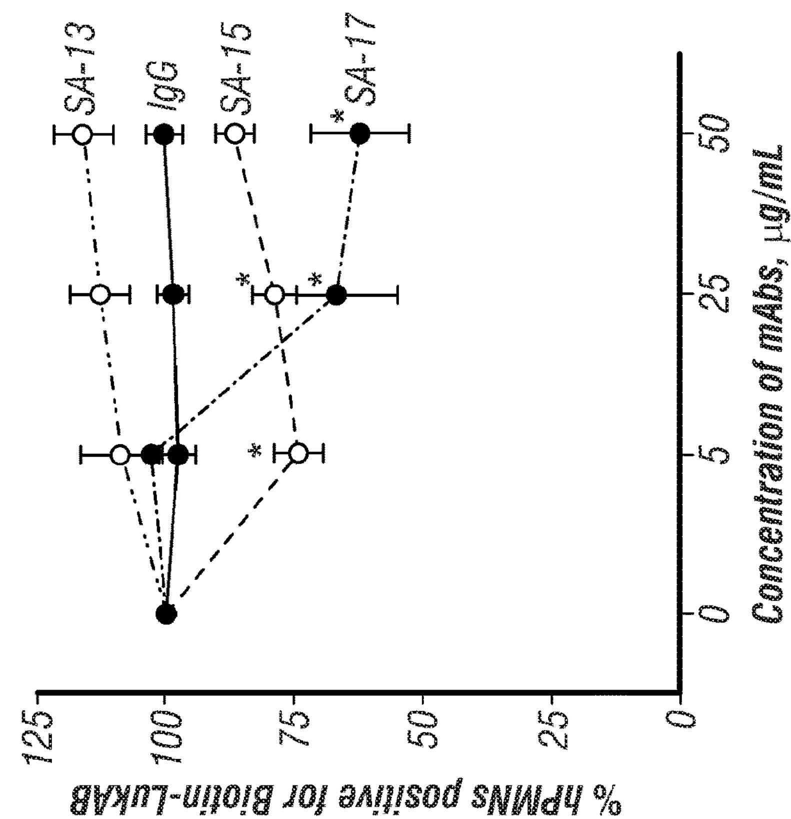

LukAB mAbs neutralize cytotoxicity using distinct mechanisms of action. The inventors next investigated the molecular mechanism by which the mAbs exerted their protective effects. First, the inventors tested whether or not the mAbs prevented association of the toxin with the surface of PMNs. Pre-incubation of LukAB with SA-17 caused a significant and titratable decrease in the amount of LukAB detected on the surface of PMNs. SA-15 also decreased LukAB-binding at two concentrations tested. SA-13, however, did not interfere with cell surface association of LukAB (FIG. 4A). Using an ELISA-based assay, the inventors demonstrated that SA-13, SA-15, and SA-17 all interfered with LukAB-binding to the human I-domain of CD11b, the host receptor for LukAB (DuMont et al., 2013a), while the IgG control did not (FIG. 4B). Consistent with the whole cell binding assays, the inventors noted varying capacities of inhibition, with SA-13 exhibiting the lowest interference of LukAB binding, despite exhibiting potent neutralization of LukAB in vitro and ex vivo.

Figure 5:
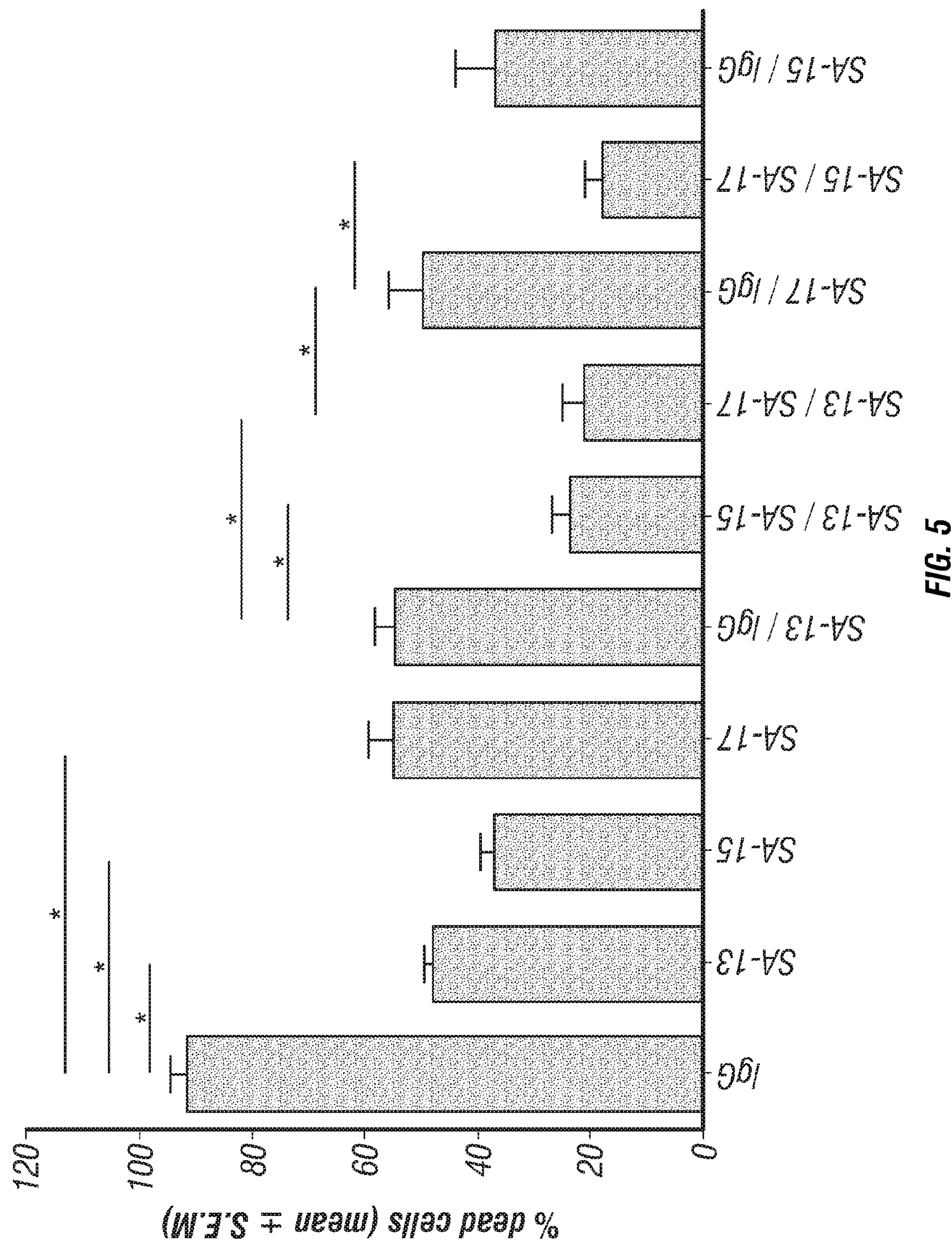
FIG. 5. LukAB mAbs exhibit enhanced neutralization when combined. MAbs were pre-incubated with LukAB (2:1 mAb:LukAB molar ratio) for 30 min at room temperature. Primary human neutrophils were added to the LukAB/antibody mixture and incubated for 1 hr. Neutrophil viability was evaluated with CellTiter. Bars represent mean±SEM, with n=6 donors. *P<0.05 using one-way ANOVA with Tukey's post hoc test correction for multiple comparisons. NS=not statistically significant.

Cooperative effects of LukAB mAb combinations for enhanced neutralization. Since the mAbs exhibited distinct patterns of recognition and mechanism of action, the inventors hypothesized that neutralization capacity could be improved using a combination of antibodies. To test this hypothesis, the inventors combined LukAB-specific or control mAbs to evaluate cooperative effects. When mixed at equal concentrations, totaling 3.2 μg/mL with a 2:1 mAb: LukAB molar ratio, they observed that antibody combinations cooperated to provide increased neutralization when compared to individual mAbs and the control (FIG. 5). SA-13 and SA-17 exhibited the strongest increase in potency when combined, while SA-15 had a more dominant individual effect. Overall, these results suggest a cooperative effect of the mAbs in combination for neutralization of the cytotoxin, presumably due to differences in binding site and mechanisms of protection.

Figure 6:
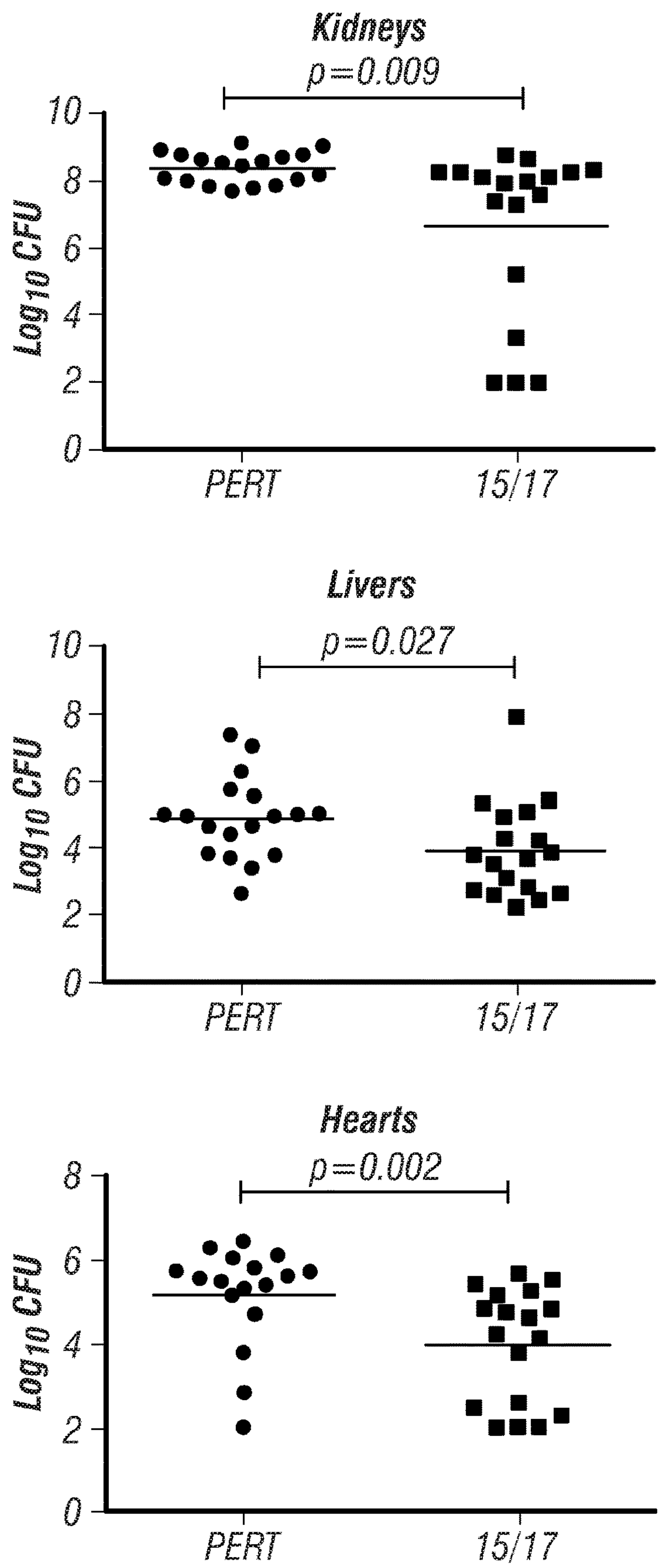
FIG. 6. In vivo protective effect of prophylactic treatment with mAbs. BALB/cJ mice were given a 1:1 mixture of SA-15 and SA-17 (1 mg/kg, i.p.) prophylactically and subjected to disseminated bacterial infection with USA300 *S. aureus*. Tissues (A: Kidneys; B: Livers; and C: Hearts) were harvested after 96 h, and bacterial load was enumerated. A significant reduction in bacterial load was observed in all three tissues compared to animals treated with a control IgG preparation.

Efficacy of anti-LukAB mAbs in vivo. While LukAB exhibits strong preferential tropism toward human leukocytes (DuMont et al., 2013a), the toxin does contribute to USA300 *S. aureus* bacterial burden in systemically infected mice (DuMont et al., 2011; Scherr et al., 2015]. Given the breadth of protection of this series of mAbs in vitro and ex vivo, the inventors investigated whether SA-15 and SA-17 protect in a murine model of *S. aureus* sepsis. A 1:1 mixture was selected due to their greater potency in intoxication experiments and was given as a single total dose of 1 mg/kg by the intraperitoneal route 20 h prior infection. This regimen resulted in significantly lower bacterial burden in murine heart, liver, and kidneys (FIG. 6) compared to the same dose of a control IgG. Interestingly, treatment with individual mAbs did not exhibit a significant protective effect, suggesting that a combination effect was required for in vivo potency.

Example 3—Discussion

In this study, the inventors report for the first time that human mAbs, isolated from the B cells of a child with invasive *Staphylococcus aureus* infection, are capable of potently neutralizing cytotoxicity mediated by LukAB. While all three mAbs neutralized the toxin, they exhibited differing levels of potency, recognized different antigenic sites, utilized distinct mechanisms of toxin inhibition, and displayed improved function when used in combination. In addition to neutralizing LukAB-mediated cytotoxicity in vitro and ex vivo, these human mAbs ameliorated disease severity in vivo. Thus, the implementation of hybridoma technology allowed the characterization of antibodies that are produced naturally during invasive human *S. aureus* disease, highlighting the utility of this approach.

The progressive increase in the prevalence of antibiotic resistance within circulating strains of *S. aureus* is well documented (Badarau et al., 2015, Sakoulas et al., 2008) and a clear need exists for novel preventive and therapeutic approaches to combat this pathogen. The vast majority of attempted staphylococcal vaccines have targeted capsular antigens and other surface components such as iron surface determinant B (Daum and Spellberg, 2012; Proctor, 2012; Thomsen et al., 2010). *S. aureus* produces a wealth of anti-antibody surface components such a Protein A and staphylokinase that impede humoral host defenses. An ideal vaccine target would be one that is expressed by all clinically important strains (both MSSA and MRSA), is important for pathogenesis, and acts extracellularly to avoid interference by surface components such as staphylococcal protein A (spa).

LukAB is increasingly recognized as a critical component of the *S. aureus* virulence repertoire devoted to evasion of human phagocytes, although its exact role during natural human infection remains to be fully elucidated. Previous studies have shown that *S. aureus* kills human phagocytes in a LukAB-dependent manner (Ventura et al., 2010; DuMont et al., 2011; Yanai et al., 2014) and that disruption of lukAB markedly impairs the ability of *S. aureus* to avoid whole blood and PMN-mediated killing (Ventura et al., 2010; DuMont et al., 2011; Melehani et al., 2014; DuMont et al., 2013a; DuMont et al., 2013b). The prominent role of LukAB in *S. aureus*-mediated killing of PMNs, the primary mediator of anti-staphylococcal host defense (Rigby et al., 2012), is greatly influenced by the increased expression of LukAB upon PMN encounter (DuMont et al., 2013a). Furthermore, the direct targeting of CD11b—a highly abundant protein on the surface of PMNs—potentiates the effect of LukAB during *S. aureus* infection DuMont et al., 2013b).

While all clinical isolates that the inventors have characterized thus far harbor the gene encoding LukAB (Thomsen et al., 2014; Chadha et al., 2016), and this toxin is expressed in various in vitro models (DuMont et al., 2011; Melehani et al., 2015; DuMont et al., 2013a; DuMont et al., 2013b; Balasubramanian et al., 2016), these observations alone do not guarantee its relevance during human disease. The inventors recently reported that anti-LukAB antibodies are produced in high titer following invasive *S. aureus* infection in children (Thomsen et al., 2014), providing strong evidence that the toxin is expressed during human disease and recognized by humoral host defenses. The human mAbs described here provide further evidence that human B cells recognize this toxin in both its monomeric and its dimerized form during invasive disease, and generate a highly functional antibody response.

Recently, Badarau et al. reported the identification of anti-LukAB antibodies by screening a large IgG library for binding to the toxin, and concluded that potent toxin neutralization required a binding site present only after toxin dimerization (Badarau et al., 2016). By contrast, the inventors found that potently neutralizing antibodies had distinct binding sites, and that naturally occurring antibodies block LukAB by targeting either the dimeric toxin or monomeric LukA. Moreover, they observed that SA-15 and SA-17 significantly inhibited toxin association with the surface of neutrophils in vitro but that SA-13 (also potently neutralizing in all in vitro assays) did not have any effect on this process. This finding suggests that SA-13 interferes with a distinct, downstream step in cytolysis such as toxin oligomerization or pore formation.

The collective results presented here suggest at least three patterns of action for anti-LukAB antibodies: 1) recognition of an epitope on the LukA monomer that blocks toxin attachment (SA-17), 2) recognition of an epitope on the LukA monomer that blocks a step in cytolysis after cell attachment (SA-13), and 3) recognition of a LukAB quaternary epitope present only on the heterodimer that interferes with receptor recognition and downstream steps in cytolysis (SA-15). The results also suggest that the functional anti-toxin antibody response following invasive human infection is diverse and indicate that toxin neutralization can be achieved by interfering with more than one step in the cytolysis pathway. In support of the latter point, the inventors observed distinct functional activity (and combination effect) among the mAbs, indicating that LukAB-mediated pore-formation and cytotoxicity can be disrupted by the host response at multiple points. Similarly, differences in mAb potency by cell type (PMN vs. macrophage-like cells) may be explained by differential mechanisms of protection (interference with receptor binding vs. interference with oligomerization/pore formation)

Altogether, this study describes the identification of novel human antibodies that potently neutralize the cytotoxic potential of *S. aureus* towards human neutrophils, and establishes an efficient workflow for the identification and purification of naturally occurring human anti-MRSA mAbs. Structure-function work, assessment of mAb function across allelic variants of LukAB, and further in vivo analyses are underway to investigate these mAbs as potential future therapeutic options to combat this major human pathogen.

TABLE 1

NUCLEOTIDE SEQUENCES FOR ANTIBODY VARIABLE REGIONS

| Clone | Variable Sequence Region | SEQ ID NO: |
|---|---|---|
| SA-13 heavy | CAGGTGCAGCTGGTGGAGTCTGGGGGAGGCTTGGTCAGGCCTGGAGGGTCCCT<br>GAGACTCTCCTGTGCAGCCTCTGGATTCACCTTCAGTGAATATTACATGAGTT<br>GGATCCGCCAGGCTCCAGGGAAGGGGCTGGAGTGGCTTTCATATATTAGCAGT<br>AGTGGTACTACCATAGGCCACGCAGACTCTCTGAAGGGCCGATTCACCATCTC<br>CAGGGACAACGCCAGGAACTCACTGTTCCTGCAAATGAATAGCCTGAGAGCCG<br>AGGACACGGCCGTCTATTACTGTGCGAGAGATGGAGTGGGGGGTCCCAGGGCG<br>AGATATGATGCTTTTGATATCTGGGGCCAAGGGACCCTGGTCACCGTCTCCTC<br>AG | 1 |
| SA-13 light | CAGTCTGTGCTGACGCAGCCGCCCTCAGTGTCTGGGGCCCCAGGGCAGAGGGT<br>CACCATCTCCTGCACTGGGACCTACTCCAACATCGGGGCAGGTTATGATGTAC<br>ACTGGTACCAACAGCTTCCAGGAAGAGCCCCCAAACTCCTCATTTATGGTAAT<br>CGGAATCGGCCCTCAGGGGTCCCTGACCGATTCTCTGGCTCCAAGTCTGGAAC<br>CTCAGCCTCCCTGGCCATCACTGGGCTCCAGGCCGAGGATGAGGCTGATTATT<br>ACTGCCAGTCCCATGACAGCAGTCTGAGTGGTTCGGTATTCGGCGGAGGGACC<br>AAGGTGACCGTCCTA | 2 |
| SA-15 heavy | CAGGTGCAGCTGGTGCAGTCTGGGGGAGGCGTGGTCCAGCCTGGGAGGTCCCT<br>AAGACTCTCCTGTGCAGCCTCTGGATTCTCCTTCAGTACCTATGACATGAACT<br>GGGTCCGCCAGGCTCCAGGCAAGGGACTGGAGTGGCTGTCAATTATATCATAT<br>GATGAAACAAATAAATACTATGCAGACTCCGTGAAGGGCCGATTCACCATCTC<br>CAGAGACAATTCCAAGAACACGCTGTTTCTGCAAATGAACAGCCTGAAACCTG<br>AGGACTCGGCTGTCTATCACTGTGTCAAAGTAGGGTGGACTCTAGTAGGTGAT<br>GGTGTTGATATGTGGGGCCAAGGGACCCTGGTCACCGTCTCCTCAG | 3 |
| SA-15 light | CAGCCTGTGCTGACTCAGTCTCCTTCCTCCCTGTCTGCGTCTGTTGGAGACAG<br>AGTCACCATCAGTTGCCGGGCGAGTCAGGGCATTAGCCATTATTTAGCCTGGT<br>ATCAGCAGCAACCAGGGAAAGTTCCTAAACTCCTGATCTATGCTGCATCCACT<br>TTGCAATCAGGGGTCCCATCTCGGTTCAGTGGCAGTGGATCTGGGACAGATTT<br>CACTCTCACCATCAGCAGCCTGCAGCCTGAAGATGTCGCAACTTATTACTGTC<br>AAAAGTATAACGGTGCCCCATTCACTTTCGGCCCTGGGACCAAAGTGGATATC<br>AAGC | 4 |
| SA-17 heavy | CAGGTGCAGCTGGTGCAGTCTGGGGGAGCCGTCGTACAGCCTGGGGGGTCCCT<br>GAGACTCTCCTGTGTAGCCTCTGGATTCACCTTTGATGATTATGCCATGCACT<br>GGGTCCGTCAAGCTCCGGGGAAGGGTCTGGAGTGGGTCTCTCTTATTACTTTG<br>GATGGTGGCCGCACATACTATGCAGACTCTGTGAAGGGTCGATTCACCATCTC<br>CAGAGACAACAGCAAGAACTCCCTGTATCTGCAAATGAACCGTCTGAGAGCTG<br>ACGACACCGGCTTCTATTACTGTGCAAGAGATATAAAGATAGGGGAAGCAGTT<br>ATGATTACTGTTCCGGGCCAACACTGGGGCCAGGGCACCCTGGTCACCGTCTC<br>CTCAG | 5 |

TABLE 1-continued

| NUCLEOTIDE SEQUENCES FOR ANTIBODY VARIABLE REGIONS | | |
|---|---|---|
| Clone | Variable Sequence Region | SEQ ID NO: |
| SA-17 light | CAGTCTGTGGTGACTCAGGACCCTGGTGTGTCTGTGGCCTTGGGACAGACAGT CTTCATCACATGCCAAGGAGACACCCTCAGAAGCAATTATGCAAACTGGTTCC AGCAGAAGCCAGGACAGGCCCCTGTCCTTGTCATGTATGGTAAAAACAACCGG CCCTCAGGGATCCCAGACCGATTCTCTGGCTCCAGCTCAGGAAACACAGCTTC CTTGACCATCACTGGGGCTCAGGCGGAAGATGAGGCTGACTATTACTGTAACT CCCGGGACAGCAGTGGTAACCATGTGGTGTTCGGCGGAGGGACCAGGGTGACC GTCCTA | 6 |
| SA-22 heavy | CAGGTGCAGCTGGTGCAGTCTGGAGGAGGCTTGATCCAGCCTGGGGGGTCCCT GAGACTGTCCTGTGCAGCCTCTGGCTTCAGCGTCAGTAGCAACTACATGAGTT GGGTCCGCCAGGCTCCAGGAAAGGGGCTGGAGTGGGTCTCAGTTATTTATAGA GATGGAACCACATATTACACAGACTCCGTGAAGGGCCGATTAACCATCTCCAG AGACATTTCCAAGAACATGGTGTACCTTCAAATGAACAGCCTAAGAGCCGAGG ACACGGCCGTGTATTACTGTGCGAGAGAGGACTCCGTGGACGGCTACTTTGAC TACTGGGGCCAGGGAACCCTGGTCACCGTCTCCTCAG | 7 |
| SA-22 light | TCCATCCTCCCTGTCTGCATCTGTAGGAGACAGAGTCGCCATCACTTGCCGGG CAAGTCAGAGCATTAGCAGGTATTTACATTGGTATCAGCAAAAACCAGGAAAA GCCCCTAAGCTCCTGATCTATGCTGCATCCAGTTTGCAAAGTGGGATCCCGTC AAGGTTCAGTGGCAGTGGAGCTGGGACAAATTTCACTCTCACCATCAGCAGTC TCCAACCTGAAGATTTTGCAACTTACTACTGTCAGGAGAGTTCCAACACCCCT CCAACTTTTGGCCAGGGGACCAAGCTGGAGATCAAAC | 8 |

TABLE 2

| PROTEIN SEQUENCES FOR ANTIBODY VARIABLE REGIONS | | |
|---|---|---|
| Clone | Variable Sequence Region | SEQ ID NO: |
| SA-13 heavy | QVQLVESGGGLVRPGGSLRLSCAASGFTFSEYYMSWIRQAPGKGLEWLSYISS SGTTIGHADSLKGRFTISRDNARNSLFLQMNSLRAEDTAVYYCARDGVGGPRA RYDAFDIWGQGTLVTVSS | 9 |
| SA-13 light | QSVLTQPPSVSGAPGQRVTISCTGTYSNIGAGYDVHWYQQLPGRAPKLLIYGN RNRPSGVPDRFSGSKSGTSASLAITGLQAEDEADYYCQSHDSSLSGSVFGGGT KVTVL | 10 |
| SA-15 heavy | QVQLVQSGGGVVQPGRSLRLSCAASGFSFSTYDMNWVRQAPGKGLEWLSIISY DETNKYYADSVKGRFTISRDNSKNTLFLQMNSLKPEDSAVYHCVKVGWTLVGD GVDMWGQGTLVTVSS | 11 |
| SA-15 light | QPVLTQSPSSLSASVGDRVTISCRASQGISHYLAWYQQQPGKVPKLLIYAAST LQSGVPSRFSGSGSGTDFTLTISSLQPEDVATYYCQKYNGAPFTFGPGTKVDI K | 12 |
| SA-17 heavy | QVQLVQSGGAVVQPGGSLRLSCVASGETFDDYAMHWVRQAPGKGLEWVSLITL DGGRTYYADSVKGRFTISRDNSKNSLYLQMNRLRADDTGFYYCARDIKIGEAV MITVPGQHWGQGTLVTVSS | 13 |
| SA-17 light | QSVVTQDPGVSVALGQTVFITCQGDTLRSNYANWFQQKPGQAPVLVMYGKNNR PSGIPDRFSGSSSGNTASLTITGAQAEDEADYYCNSRDSSGNHVVFGGGTRVT VL | 14 |
| SA-22 heavy | QVQLVQSGGGLIQPGGSLRLSCAASGFSVSSNYMSWVRQAPGKGLEWVSVIYR DGTTYYTDSVKGRLTISRDISKNMVYLQMNSLRAEDTAVYYCAREDSVDGYFD YWGQGTLVTVSS | 15 |
| SA-22 light | PSSLSASVGDRVAITCRASQSISRYLHWYQQKPGKAPKLLIYAASSLQSGIPS RFSGSGAGTNFTLTISSLQPEDFATYYCQESSNTPPTFGQGTKLEIK | 16 |

TABLE 3

| CDR HEAVY CHAIN SEQUENCES | | | |
|---|---|---|---|
| Antibody | CDRH1 (SEQ ID NO:) | CDRH2 (SEQ ID NO:) | CDRH3 (SEQ ID NO:) |
| SA-13 | GFTFSEYY (17) | ISSSGTTI (18) | CARDGVGGPRARYDAFDIW (19) |
| SA-15 | GFSFSTYD (20) | ISYDETNK (21) | CVKVGWTLVGDGVDMW (22) |
| SA-17 | GFTFDDYA (23) | ITLDGGRT (24) | CARDIKIGEAVMITVPGQHW (25) |
| SA-22 | GFSVSSNY (26) | IYRDGTT (27) | CAREDSVDGYFDYW (28) |

TABLE 4

| CDR LIGHT CHAIN SEQUENCES | | | |
|---|---|---|---|
| Antibody | CDRL1 (SEQ ID NO:) | CDRL2 (SEQ ID NO:) | CDRL3 (SEQ ID NO:) |
| SA-13 | YSNIGAGYD (29) | GNR (30) | CQSHDSSLSGSVF (31) |
| SA-15 | QGISHY (32) | AAS (33) | CQKYNGAPFTF (34) |
| SA-17 | TLRSNY (35) | GKN (36) | CNSRDSSGNHVVF (37) |
| SA-22 | QSISRY (38) | AAS (39) | CQESSNTPPTF (40) |

TABLE S1

GENETIC CHARACTERISTICS OF ANTI-LUKAB ANTIBODIES
Supplemental Table 1. Genetic characteristics of anti-LukAB antibodies

| mab | Isotype | $EC_{50}$[1] (μg/mL) | Heavy chain V gene | J gene | D gene | Number of AA In CDR1 | CDR2 | CDR3 | HCDR3 AA sequence | Nt mutations | AA mutations |
|---|---|---|---|---|---|---|---|---|---|---|---|
| SA-13 | IgG2, λ | 0.8 | 3-11*01 | 3*02 | 2-15*01 | 8 | 8 | 17 | CARDGVGGPRARYDAFDIW | 19 | 11 |
| SA-15 | IgG1, κ | 1.5 | 3-30*03 | 3*02 | 6-13*01 | 8 | 8 | 14 | CVRVGWTLVGDGVIMW | 27 | 20 |
| SA-17 | IgG1, λ | 0.3 | 3-430*01 | 1*01 | 5-18*01 | 8 | 8 | 18 | CARDIKIGEAVMITQPGQHW | 23 | 17 |
| SA-22 | IgG1, κ | — | V3-53*01 | 4*02 | 4-17*01 | 8 | 7 | 12 | CAREDGVDGYFDYW | 22 | 13 |

| mab | Light Chain V gene | J gene | Number of AA In CDR1 | CDR2 | CDR3 | LCDR3 AA sequence | Nt mutations | AA mutations |
|---|---|---|---|---|---|---|---|---|
| SA-13 | # | | | | | | | |
| SA-15 | KV1-27*01 | KI3*01 | 6 | 3 | 9 | CQKYNGAPFTF | 19 | 8 |
| SA-17 | KV1-39*01 | KI2*01 | 6 | 3 | 9 | CQESSNTPPTF | 16 | 11 |
| SA-22 | LV3-19*01 | LI2*01 | 6 | 3 | 11 | CNSRDSSGNHVVF | 15 | 12 |

SA-13 was obtained from acute sample, while SA-15 and SA-17 were obtained from the convalescent sample.

[1]$EC_{50}$ values were obtained in ELISA with LukAB as the antigen. SA-22 was obtained from the same patient, but recognizes IsdA, another *S. aureus* protein.

We were not able to obtain the sequence of variable domain of the light chain.

Nt = nucleotide; AA = amino acid; CDR = Complementarity Determining Region (SEQ ID NO: 19)

(SEQ ID NO: 22) (SEQ ID NO: 34)

(SEQ ID NO: 25) (SEQ ID NO: 40)

(SEQ ID NO: 28) (SEQ ID NO: 37)

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

"Antibodies: A Laboratory Manual," Cold Spring Harbor Press, Cold Spring Harbor, N.Y., 1988.

Abbondanzo et al., *Am. J. Pediatr. Hematol. Oncol.,* 12(4), 480-489, 1990.

Allred et al., *Arch. Surg.,* 125(1), 107-113, 1990.

Atherton et al., *Biol. of Reproduction,* 32, 155-171, 1985.

Badarau A, Rouha H, Malafa S, et al. Structure-function analysis of heterodimer formation, oligomerization, and receptor binding of the *Staphylococcus aureus* bicomponent toxin LukGH. J Biol Chem [Internet]. 2015; 290(1): 142-56.

Badarau A, Rouha H, Malafa S, et al. Context matters: The importance of dimerization-induced conformation of the LukGH leukocidin of *Staphylococcus aureus* for the generation of neutralizing antibodies. MAbs [Internet]. 2016; 142(1):75-85.

Balasubramanian D, Ohneck E A, Chapman J, et al. *Staphylococcus aureus* Coordinates Leukocidin Expression and Pathogenesis by Sensing Metabolic Fluxes via RpiRc. MBio [Internet]. 2016; 7(3):1130-3.

Boles B R, Thoendel M, Roth A J, Horswill A R. Identification of genes involved in polysaccharide-independent *Staphylococcus aureus* biofilm formation. PLoS One [Internet]. 2010; 5(4):e10146.

Brochet X, Lefranc M P, Giudicelli V. IMGT/V-QUEST: the highly customized and integrated system for IG and TR standardized V-J and V-D-J sequence analysis. Nucleic Acids Res 2008; 36:W503-8.

Brown et al., *J. Immunol. Meth.,* 12; 130(1), :111-121, 1990.

Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.

Capaldi et al., *Biochem. Biophys. Res. Comm.,* 74(2):425-433, 1977.

Chadha A D, Thomsen I P, Jimenez-Truque N, et al. Host response to *Staphylococcus aureus* cytotoxins in children with cystic fibrosis. J Cyst Fibros [Internet]. 2016.

Daum R S, Spellberg B. Progress toward a *Staphylococcus aureus* vaccine. Clin Infect Dis. 2012; 54(4):560-567.

De Jager et al., *Semin. Nucl. Med.* 23(2), 165-179, 1993.

Dholakia et al., *J. Biol. Chem.,* 264, 20638-20642, 1989.

Diep B A, Gill S R, Chang R F, et al. Complete genome sequence of USA300, an epidemic clone of community-acquired meticillin-resistant *Staphylococcus aureus*. Lancet. 2006; 367(9512):731-739.

Doolittle and Ben-Zeev, *Methods Mol. Biol.,* 109, 215-237, 1999.

DuMont A L, Nygaard T K, Watkins R L, et al. Characterization of a new cytotoxin that contributes to *Staphylococcus aureus* pathogenesis. Mol Microbiol. 2011; 79(3): 814-825.

DuMont A L, Yoong P, Surewaard B G J, et al. *Staphylococcus aureus* elaborates leukocidin A B to mediate escape from within human neutrophils. Infect Immun. 2013a; 81(5):1830-1841.

DuMont A L, Yoong P, Day C J, et al. *Staphylococcus aureus* LukAB cytotoxin kills human neutrophils by targeting the CD11 b subunit of the integrin Mac-1. Proc Natl Acad Sci USA [Internet]. 2013b; 110(26):10794-9.

DuMont A L, Yoong P, Liu X, et al. *Identification of a crucial residue required for Staphylococcus aureus* LukAB cytotoxicity and receptor recognition. Infect Immun. 2014; 82(3):1268-1276.

Flyak A I, Ilinykh P A, Murin C D, et al. Mechanism of human antibody-mediated neutralization of Marburg virus. Cell [Internet]. 2015; 160(5):893-903.

Gefter et al., *Somatic Cell Genet.,* 3:231-236, 1977.

Gulbis and Galand, *Hum. Pathol.* 24(12), 1271-1285, 1993.

Hammer N D, Reniere M L, Cassat J E, et al. Two heme-dependent terminal oxidases power *Staphylococcus aureus* organ-specific colonization of the vertebrate host. MBio. 2013; 4(4).

Khatoon et al., *Ann. of Neurology,* 26, 210-219, 1989.

Kehl-Fie T E, Zhang Y, Moore J L, et al. *MntABC and MntH contribute to systemic Staphylococcus aureus* infection by competing with calprotectin for nutrient manganese. *Infect Immun.* 2013; 81(9):3395-3405.

King et al., *J. Biol. Chem.,* 269, 10210-10218, 1989.

Kohler and Milstein, *Eur. J. Immunol.,* 6, 511-519, 1976.

Kohler and Milstein, *Nature,* 256, 495-497, 1975.

Kyte and Doolittle, *J. Mol. Biol.,* 157(1):105-132, 1982.

Melehani J H, James D B A, DuMont A L, Tones V J, Duncan J A. *Staphylococcus aureus* Leukocidin A/B (LukAB) Kills Human Monocytes via Host NLRP3 and ASC when Extracellular, but Not Intracellular. PLOS Pathog [Internet]. 2015; 11(6):e1004970.

Nakamura et al., *In: Enzyme Immunoassays: Heterogeneous and Homogeneous Systems*, Chapter 27, 1987.

O'Shannessy et al., *J. Immun. Meth.,* 99, 153-161, 1987.

Park E K, Jung H S, Yang H I, Yoo M C, Kim C, Kim K S. Optimized THP-1 differentiation is required for the detection of responses to weak stimuli. *Inflamm Res* 2007; 56:45-50.

Persic et al., *Gene* 187:1, 1997

Potter and Haley, *Meth. Enzymol.,* 91, 613-633, 1983.

Proctor R. A., Is there a future for a *Staphylococcus aureus* vaccine? Vaccine [Internet]. 2012; 30(19):2921-7.

*Remington's Pharmaceutical Sciences,* 15th Ed., 3:624-652, 1990.

Reyes-Robles T, Lubkin A, Alonzo F, 3rd, Lacy D B, Torres V J. Exploiting dominant-negative toxins to combat *Staphylococcus aureus* pathogenesis. EMBO Rep 2016; 17:428-40.

Rigby K M, DeLeo F R. Neutrophils in innate host defense against *Staphylococcus aureus* infections. Semin Immunopathol [Internet]. 2012; 34(2):237-59.

Sakoulas G, Moellering R C. Increasing antibiotic resistance among methicillin-resistant *Staphylococcus aureus* strains. *Clin Infect Dis.* 2008; 46 Suppl 5(Suppl 5):5360-5367.

Scherr T D, Hanke M L, Huang 0, et al. *Staphylococcus aureus* biofilms induce macrophage dysfunction through leukocidin AB and alpha-toxin. MBio. 2015; 6(4).

Tang et al., *J. Biol. Chem.,* 271:28324-28330, 1996.

Thomsen I P, DuMont A L, James D B A, et al. Children with invasive *Staphylococcus aureus* disease exhibit a potently neutralizing antibody response to the cytotoxin LukAB. Infect Immun. 2014; 82(3):1234-1242.

Thomsen I, Dudney H, Creech C B. Searching for the holy grail of a staphylococcal vaccine. Hum Vaccin. 2010; 6(12):1068-1070.

Thornburg N J, Zhang H, Bangaru S, et al. H7N9 influenza virus neutralizing antibodies that possess few somatic mutations. J Clin Invest 2016; 126:1482-94.

Ueda T, Rieu P, Brayer J, Arnaout M A. Identification of the complement iC3b binding site in the beta 2 integrin CR3 (CD11b/CD18). *Proc Natl Acad Sci USA* [Internet]. 1994; 91(22): 10680-4.

U.S. Pat. No. 3,817,837

U.S. Pat. No. 3,850,752

U.S. Pat. No. 3,939,350

U.S. Pat. No. 3,996,345

U.S. Pat. No. 4,196,265

U.S. Pat. No. 4,275,149

U.S. Pat. No. 4,277,437

U.S. Pat. No. 4,366,241

U.S. Pat. No. 4,472,509

U.S. Pat. No. 4,554,101

U.S. Pat. No. 4,680,338

U.S. Pat. No. 4,816,567

U.S. Pat. No. 4,867,973

U.S. Pat. No. 4,938,948

U.S. Pat. No. 5,021,236

U.S. Pat. No. 5,141,648

U.S. Pat. No. 5,196,066

U.S. Pat. No. 5,563,250

U.S. Pat. No. 5,565,332

U.S. Pat. No. 5,856,456

U.S. Pat. No. 5,880,270

Ventura C L, Malachowa N, Hammer C H, et al. Identification of a novel *Staphylococcus aureus* two-component leukotoxin using cell surface proteomics. *PLoS One.* 2010; 5(7).

Wawrzynczak & Thorpe, In: *Immunoconjugates, Antibody Conuugates In Radioimaging And Therapy Of Cancer*, Vogel (Ed.), N Y, Oxford University Press, 28, 1987.

Wright, A. E., Notes on the Treatment of Furunculosis, Sycosis, and Acne by the Inoculation of a *Staphylococcus aureus* Vaccine. *Lancet.* 1902; 159(4100):874-884.

Yanai M, Rocha M A, Matolek A Z, et al. Separately or combined, LukG/LukH is functionally unique compared to other staphylococcal bicomponent leukotoxins. PLoS One [Internet]. 2014 9(2):e89308.

Yu et al., An optimized electrofusion-based protocol for generating virus-specific human monoclonal antibodies. *J Immunol Methods* 336(2):142-151, 2008.

What is claimed is:

1. A method of treating a subject infected with *Staphylococcus aureus*, or reducing the likelihood of infection of a subject at risk of contracting *Staphylococcus aureus*, comprising delivering to said subject an antibody or antibody fragment having (a) heavy chain CDR1, CDR2 and CDR3 of SEQ ID NOS: 17, 18 and 19, and light chain CDR1, CDR2 and CDR3 of SEQ ID NOS: 29, 30 and 31; (b) heavy chain CDR1, CDR2 and CDR3 of SEQ ID NOS: 20, 21 and 22, and light chain CDR1, CDR2 and CDR3 of SEQ ID NOS: 32, 33 and 34; (c) heavy chain CDR1, CDR2 and CDR3 of SEQ ID NOS: 23, 24 and 25, and light chain CDR1, CDR2 and CDR3 of SEQ ID NOS: 35, 36 and 37; or (d) heavy chain CDR1, CDR2 and CDR3 of SEQ ID NOS: 26, 27 and 28, and light chain CDR1, CDR2 and CDR3 of SEQ ID NOS: 38, 39 and 40.

2. The method of claim 1, wherein the antibody or antibody fragment is encoded by heavy and light chain variable sequences SEQ ID NOS: 1 and 2, SEQ ID NOS: 3 and 4, SEQ ID NOS: 5 and 6, or SEQ ID NOS: 7 and 8, respectively.

3. The method of claim 1, wherein said antibody or antibody fragment is encoded by heavy and light chain variable sequences having 70%, 80%, or 90% identity to heavy and light chain variable sequences SEQ ID NOS: 1 and 2, SEQ ID NOS: 3 and 4, SEQ ID NOS: 5 and 6, or SEQ ID NOS: 7 and 8, respectively.

4. The method of claim 1, wherein said antibody or antibody fragment is encoded by heavy and light chain variable sequences having 95% identity to heavy and light chain variable sequences SEQ ID NOS: 1 and 2, SEQ ID NOS: 3 and 4, SEQ ID NOS: 5 and 6, or SEQ ID NOS: 7 and 8, respectively.

5. The method of 1, wherein said antibody or antibody fragment comprises heavy and light chain variable sequences heavy and light chain variable sequences SEQ ID NOS: 9 and 10, SEQ ID NOS: 11 and 12, SEQ ID NOS: 13 and 14, or SEQ ID NOS: 15 and 16, respectively.

6. The method of claim 1, wherein said antibody or antibody fragment comprises heavy and light chain variable sequences having 70%, 80% or 90% identity to heavy and light chain variable sequences SEQ ID NOS: 9 and 10, SEQ ID NOS: 11 and 12, SEQ ID NOS: 13 and 14, or SEQ ID NOS: 15 and 16, respectively.

7. The method of claim 1, wherein said antibody or antibody fragment comprises heavy and light chain variable sequences having 95% identity to heavy and light chain variable sequences as SEQ ID NOS: 9 and 10, SEQ ID NOS: 11 and 12, SEQ ID NOS: 13 and 14, or SEQ ID NOS: 15 and 16, respectively.

8. The method of claim 1, wherein the antibody fragment is a recombinant scFv (single chain fragment variable) antibody, Fab fragment, $F(ab')_2$ fragment, or Fv fragment, a chimeric antibody and/or is an IgG.

9. The method of claim 1, wherein said antibody or antibody fragment recognizes an epitope exclusively found on LukAB, or an epitope found on LukA and LukAB, and/or inhibits LukAB-binding to the human I-domain of CD11b.

10. The method of claim 9, wherein said antibody or antibody fragment reduces the toxicity of LukAB.

11. The method of claim 1, wherein said antibody or antibody fragment is administered prior to infection.

12. The method of claim 1, wherein said antibody or antibody fragment is administered after infection.

13. The method of claim 1, wherein delivering comprises antibody or antibody fragment administration, or genetic delivery with an RNA or DNA sequence or vector encoding the antibody or antibody fragment.

* * * * *

SEQUENCE LISTING

<160> NUMBER OF SEQ ID NOS: 41

<210> SEQ ID NO 1
<211> LENGTH: 373
<212> TYPE: DNA
<213> ORGANISM: Artificial sequence
<220> FEATURE:
<223> OTHER INFORMATION: Synthetic oligonucleotide

<400> SEQUENCE: 1
caggtgcagc tggtggagtc tgggggaggc ttggtcaggc ctggagggtc cctgagactc 60
tcctgtgcag cctctggatt caccttcagt gaatattaca tgagttggat ccgccaggct 120
ccagggaagg ggctggagtg gctttcatat attagcagta gtggtactac cataggccac 180
gcagactctc tgaagggccg attcaccatc tccagggaca acgccaggaa ctcactgttc 240
ctgcaaatga atagcctgag agccgaggac acggccgtct attactgtgc gagagatgga 300
gtggggggtc ccagggcgag atatgatgct tttgatatct ggggccaagg gaccctggtc 360
accgtctcct cag 373

<210> SEQ ID NO 2
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 2
cagtctgtgc tgacgcagcc gccctcagtg tctggggccc cagggcagag ggtcaccatc 60
tcctgcactg ggacctactc caacatcggg gcaggttatg atgtacactg gtaccaacag 120
cttccaggaa gagcccccaa actcctcatt tatggtaatc ggaatcggcc ctcaggggtc 180
cctgaccgat tctctggctc caagtctgga acctcagcct ccctggccat cactgggctc 240

```
caggccgagg atgaggctga ttattactgc cagtcccatg acagcagtct gagtggttcg    300

gtattcggcg gagggaccaa ggtgaccgtc cta                                 333
```

<210> SEQ ID NO 3
<211> LENGTH: 364
<212> TYPE: DNA
<213> ORGANISM: Artificial sequence
<220> FEATURE:
<223> OTHER INFORMATION: Synthetic oligonucleotide

<400> SEQUENCE: 3

```
caggtgcagc tggtgcagtc tgggggaggc gtggtccagc ctgggaggtc cctaagactc     60

tcctgtgcag cctctggatt ctccttcagt acctatgaca tgaactgggt ccgccaggct    120

ccaggcaagg gactggagtg gctgtcaatt atatcatatg atgaaacaaa taaatactat    180

gcagactccg tgaagggccg attcaccatc tccagagaca attccaagaa cacgctgttt    240

ctgcaaatga acagcctgaa acctgaggac tcggctgtct atcactgtgt caaagtaggg    300

tggactctag taggtgatgg tgttgatatg tggggccaag ggaccctggt caccgtctcc    360

tcag                                                                 364
```

<210> SEQ ID NO 4
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 4

```
cagcctgtgc tgactcagtc tccttcctcc ctgtctgcgt ctgttggaga cagagtcacc     60

atcagttgcc gggcgagtca gggcattagc cattatttag cctggtatca gcagcaacca    120

gggaaagttc ctaaactcct gatctatgct gcatccactt tgcaatcagg ggtcccatct    180

cggttcagtg gcagtggatc tgggacagat ttcactctca ccatcagcag cctgcagcct    240

gaagatgtcg caacttatta ctgtcaaaag tataacggtg ccccattcac tttcggccct    300

gggaccaaag tggatatcaa gc                                             322
```

<210> SEQ ID NO 5
<211> LENGTH: 376
<212> TYPE: DNA
<213> ORGANISM: Artificial sequence
<220> FEATURE:
<223> OTHER INFORMATION: Synthetic oligonucleotide

<400> SEQUENCE: 5

```
caggtgcagc tggtgcagtc tggggGagcc gtcgtacagc ctggggggtc cctgagactc     60

tcctgtgtag cctctggatt cacctttgat gattatgcca tgcactgggt ccgtcaagct    120

ccggggaagg gtctggagtg ggtctctctt attactttgg atggtggccg cacatactat    180

gcagactctg tgaagggtcg attcaccatc tccagagaca acagcaagaa ctccctgtat    240

ctgcaaatga accgtctgag agctgacgac accggcttct attactgtgc aagagatata    300

aagatagggg aagcagttat gattactgtt ccgggccaac actggggcca gggcaccctg    360

gtcaccgtct cctcag                                                    376
```

<210> SEQ ID NO 6
<211> LENGTH: 324
<212> TYPE: DNA

<213> ORGANISM: Artificial sequence
<220> FEATURE:
<223> OTHER INFORMATION: Synthetic oligonucleotide

<400> SEQUENCE: 6

```
cagtctgtgg tgactcagga ccctggtgtg tctgtggcct tgggacagac agtcttcatc     60

acatgccaag gagacaccct cagaagcaat tatgcaaact ggttccagca gaagccagga    120

caggcccctg tccttgtcat gtatggtaaa aacaaccggc cctcagggat cccagaccga    180

ttctctggct ccagctcagg aaacacagct tccttgacca tcactggggc tcaggcggaa    240

gatgaggctg actattactg taactcccgg gacagcagtg gtaaccatgt ggtgttcggc    300

ggagggacca gggtgaccgt ccta                                           324
```

<210> SEQ ID NO 7
<211> LENGTH: 355
<212> TYPE: DNA
<213> ORGANISM: Artificial sequence
<220> FEATURE:
<223> OTHER INFORMATION: Synthetic oligonucleotide

<400> SEQUENCE: 7

```
caggtgcagc tggtgcagtc tggaggaggc ttgatccagc ctgggggggtc cctgagactg     60

tcctgtgcag cctctggctt cagcgtcagt agcaactaca tgagttgggt ccgccaggct    120

ccaggaaagg ggctggagtg ggtctcagtt atttatagag atggaaccac atattacaca    180

gactccgtga agggccgatt aaccatctcc agagacattt ccaagaacat ggtgtacctt    240

caaatgaaca gcctaagagc cgaggacacg gccgtgtatt actgtgcgag agaggactcc    300

gtggacggct actttgacta ctggggccag ggaaccctgg tcaccgtctc ctcag         355
```

<210> SEQ ID NO 8
<211> LENGTH: 302
<212> TYPE: DNA
<213> ORGANISM: Artificial sequence
<220> FEATURE:
<223> OTHER INFORMATION: Synthetic oligonucleotide

<400> SEQUENCE: 8

```
tccatcctcc ctgtctgcat ctgtaggaga cagagtcgcc atcacttgcc gggcaagtca     60

gagcattagc aggtatttac attggtatca gcaaaaacca ggaaaagccc ctaagctcct    120

gatctatgct gcatccagtt tgcaaagtgg gatcccgtca aggttcagtg gcagtggagc    180

tgggacaaat ttcactctca ccatcagcag tctccaacct gaagattttg caacttacta    240

ctgtcaggag agttccaaca cccctccaac ttttggccag gggaccaagc tggagatcaa    300

ac                                                                   302
```

<210> SEQ ID NO 9
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 9

```
Gln Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Glu Tyr
            20                  25                  30

Tyr Met Ser Trp Ile Arg Gln Ala Pro Gly Lys Gly Leu Glu Trp Leu
```

```
        35                  40                  45

Ser Tyr Ile Ser Ser Ser Gly Thr Thr Ile Gly His Ala Asp Ser Leu
    50                  55                  60

Lys Gly Arg Phe Thr Ile Ser Arg Asp Asn Ala Arg Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gly Val Gly Gly Pro Arg Ala Arg Tyr Asp Ala Phe Asp
            100                 105                 110

Ile Trp Gly Gln Gly Thr Leu Val Thr Val Ser Ser
        115                 120


<210> SEQ ID NO 10
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 10

Gln Ser Val Leu Thr Gln Pro Pro Ser Val Ser Gly Ala Pro Gly Gln
1               5                   10                  15

Arg Val Thr Ile Ser Cys Thr Gly Thr Tyr Ser Asn Ile Gly Ala Gly
            20                  25                  30

Tyr Asp Val His Trp Tyr Gln Gln Leu Pro Gly Arg Ala Pro Lys Leu
        35                  40                  45

Leu Ile Tyr Gly Asn Arg Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser His Asp Ser Ser
                85                  90                  95

Leu Ser Gly Ser Val Phe Gly Gly Gly Thr Lys Val Thr Val Leu
            100                 105                 110


<210> SEQ ID NO 11
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 11

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Ser Phe Ser Thr Tyr
            20                  25                  30

Asp Met Asn Trp Val Arg Gln Ala Pro Gly Lys Gly Leu Glu Trp Leu
        35                  40                  45

Ser Ile Ile Ser Tyr Asp Glu Thr Asn Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Lys Pro Glu Asp Ser Ala Val Tyr His Cys
                85                  90                  95

Val Lys Val Gly Trp Thr Leu Val Gly Asp Gly Val Asp Met Trp Gly
            100                 105                 110
```

```
Gln Gly Thr Leu Val Thr Val Ser Ser
        115                 120


<210> SEQ ID NO 12
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 12

Gln Pro Val Leu Thr Gln Ser Pro Ser Ser Leu Ser Ala Ser Val Gly
1               5                   10                  15

Asp Arg Val Thr Ile Ser Cys Arg Ala Ser Gln Gly Ile Ser His Tyr
            20                  25                  30

Leu Ala Trp Tyr Gln Gln Gln Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Gly Ala Pro Phe
                85                  90                  95

Thr Phe Gly Pro Gly Thr Lys Val Asp Ile Lys
            100                 105


<210> SEQ ID NO 13
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 13

Gln Val Gln Leu Val Gln Ser Gly Gly Ala Val Val Gln Pro Gly Gly
1               5                   10                  15

Ser Leu Arg Leu Ser Cys Val Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Thr Leu Asp Gly Gly Arg Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Arg Leu Arg Ala Asp Asp Thr Gly Phe Tyr Tyr Cys
                85                  90                  95

Ala Arg Asp Ile Lys Ile Gly Glu Ala Val Met Ile Thr Val Pro Gly
            100                 105                 110

Gln His Trp Gly Gln Gly Thr Leu Val Thr Val Ser Ser
        115                 120                 125


<210> SEQ ID NO 14
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 14

Gln Ser Val Val Thr Gln Asp Pro Gly Val Ser Val Ala Leu Gly Gln
```

```
1               5                   10                  15

Thr Val Phe Ile Thr Cys Gln Gly Asp Thr Leu Arg Ser Asn Tyr Ala
            20                  25                  30

Asn Trp Phe Gln Gln Lys Pro Gly Gln Ala Pro Val Leu Val Met Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Arg Val Thr Val Leu
            100                 105


<210> SEQ ID NO 15
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 15

Gln Val Gln Leu Val Gln Ser Gly Gly Gly Leu Ile Gln Pro Gly Gly
1               5                   10                  15

Ser Leu Arg Leu Ser Cys Ala Ala Ser Gly Phe Ser Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Arg Asp Gly Thr Thr Tyr Tyr Thr Asp Ser Val Lys
    50                  55                  60

Gly Arg Leu Thr Ile Ser Arg Asp Ile Ser Lys Asn Met Val Tyr Leu
65                  70                  75                  80

Gln Met Asn Ser Leu Arg Ala Glu Asp Thr Ala Val Tyr Tyr Cys Ala
                85                  90                  95

Arg Glu Asp Ser Val Asp Gly Tyr Phe Asp Tyr Trp Gly Gln Gly Thr
            100                 105                 110

Leu Val Thr Val Ser Ser
        115


<210> SEQ ID NO 16
<211> LENGTH: 100
<212> TYPE: PRT
<213> ORGANISM: Artificial sequence
<220> FEATURE:
<223> OTHER INFORMATION: Synthetic polypeptide

<400> SEQUENCE: 16

Pro Ser Ser Leu Ser Ala Ser Val Gly Asp Arg Val Ala Ile Thr Cys
1               5                   10                  15

Arg Ala Ser Gln Ser Ile Ser Arg Tyr Leu His Trp Tyr Gln Gln Lys
            20                  25                  30

Pro Gly Lys Ala Pro Lys Leu Leu Ile Tyr Ala Ala Ser Ser Leu Gln
        35                  40                  45

Ser Gly Ile Pro Ser Arg Phe Ser Gly Ser Gly Ala Gly Thr Asn Phe
    50                  55                  60

Thr Leu Thr Ile Ser Ser Leu Gln Pro Glu Asp Phe Ala Thr Tyr Tyr
65                  70                  75                  80
```

```
Cys Gln Glu Ser Ser Asn Thr Pro Pro Thr Phe Gly Gln Gly Thr Lys
                85                  90                  95

Leu Glu Ile Lys
            100


<210> SEQ ID NO 17
<211> LENGTH: 8
<212> TYPE: PRT
<213> ORGANISM: Artificial sequence
<220> FEATURE:
<223> OTHER INFORMATION: Synthetic peptide

<400> SEQUENCE: 17

Gly Phe Thr Phe Ser Glu Tyr Tyr
1               5


<210> SEQ ID NO 18
<211> LENGTH: 8
<212> TYPE: PRT
<213> ORGANISM: Artificial sequence
<220> FEATURE:
<223> OTHER INFORMATION: Synthetic peptide

<400> SEQUENCE: 18

Ile Ser Ser Ser Gly Thr Thr Ile
1               5


<210> SEQ ID NO 19
<211> LENGTH: 19
<212> TYPE: PRT
<213> ORGANISM: Artificial sequence
<220> FEATURE:
<223> OTHER INFORMATION: Synthetic peptide

<400> SEQUENCE: 19

Cys Ala Arg Asp Gly Val Gly Gly Pro Arg Ala Arg Tyr Asp Ala Phe
1               5                   10                  15

Asp Ile Trp


<210> SEQ ID NO 20
<211> LENGTH: 8
<212> TYPE: PRT
<213> ORGANISM: Artificial sequence
<220> FEATURE:
<223> OTHER INFORMATION: Synthetic peptide

<400> SEQUENCE: 20

Gly Phe Ser Phe Ser Thr Tyr Asp
1               5


<210> SEQ ID NO 21
<211> LENGTH: 8
<212> TYPE: PRT
<213> ORGANISM: Artificial sequence
<220> FEATURE:
<223> OTHER INFORMATION: Synthetic peptide

<400> SEQUENCE: 21

Ile Ser Tyr Asp Glu Thr Asn Lys
1               5


<210> SEQ ID NO 22
<211> LENGTH: 16
<212> TYPE: PRT
<213> ORGANISM: Artificial sequence
<220> FEATURE:
```

<223> OTHER INFORMATION: Synthetic peptide

<400> SEQUENCE: 22

```
Cys Val Lys Val Gly Trp Thr Leu Val Gly Asp Gly Val Asp Met Trp
1               5                   10                  15
```

<210> SEQ ID NO 23
<211> LENGTH: 8
<212> TYPE: PRT
<213> ORGANISM: Artificial sequence
<220> FEATURE:
<223> OTHER INFORMATION: Synthetic peptide

<400> SEQUENCE: 23

```
Gly Phe Thr Phe Asp Asp Tyr Ala
1               5
```

<210> SEQ ID NO 24
<211> LENGTH: 8
<212> TYPE: PRT
<213> ORGANISM: Artificial sequence
<220> FEATURE:
<223> OTHER INFORMATION: Synthetic peptide

<400> SEQUENCE: 24

```
Ile Thr Leu Asp Gly Gly Arg Thr
1               5
```

<210> SEQ ID NO 25
<211> LENGTH: 20
<212> TYPE: PRT
<213> ORGANISM: Artificial sequence
<220> FEATURE:
<223> OTHER INFORMATION: Synthetic peptide

<400> SEQUENCE: 25

```
Cys Ala Arg Asp Ile Lys Ile Gly Glu Ala Val Met Ile Thr Val Pro
1               5                   10                  15

Gly Gln His Trp
            20
```

<210> SEQ ID NO 26
<211> LENGTH: 8
<212> TYPE: PRT
<213> ORGANISM: Artificial sequence
<220> FEATURE:
<223> OTHER INFORMATION: Synthetic peptide

<400> SEQUENCE: 26

```
Gly Phe Ser Val Ser Ser Asn Tyr
1               5
```

<210> SEQ ID NO 27
<211> LENGTH: 7
<212> TYPE: PRT
<213> ORGANISM: Artificial sequence
<220> FEATURE:
<223> OTHER INFORMATION: Synthetic peptide

<400> SEQUENCE: 27

```
Ile Tyr Arg Asp Gly Thr Thr
1               5
```

<210> SEQ ID NO 28
<211> LENGTH: 14
<212> TYPE: PRT

```
<213> ORGANISM: Artificial sequence
<220> FEATURE:
<223> OTHER INFORMATION: Synthetic peptide

<400> SEQUENCE: 28

Cys Ala Arg Glu Asp Ser Val Asp Gly Tyr Phe Asp Tyr Trp
1               5                   10


<210> SEQ ID NO 29
<211> LENGTH: 9
<212> TYPE: PRT
<213> ORGANISM: Artificial sequence
<220> FEATURE:
<223> OTHER INFORMATION: Synthetic peptide

<400> SEQUENCE: 29

Tyr Ser Asn Ile Gly Ala Gly Tyr Asp
1               5


<210> SEQ ID NO 30
<211> LENGTH: 3
<212> TYPE: PRT
<213> ORGANISM: Artificial sequence
<220> FEATURE:
<223> OTHER INFORMATION: Synthetic peptide

<400> SEQUENCE: 30

Gly Asn Arg
1


<210> SEQ ID NO 31
<211> LENGTH: 13
<212> TYPE: PRT
<213> ORGANISM: Artificial sequence
<220> FEATURE:
<223> OTHER INFORMATION: Synthetic peptide

<400> SEQUENCE: 31

Cys Gln Ser His Asp Ser Ser Leu Ser Gly Ser Val Phe
1               5                   10


<210> SEQ ID NO 32
<211> LENGTH: 6
<212> TYPE: PRT
<213> ORGANISM: Artificial sequence
<220> FEATURE:
<223> OTHER INFORMATION: Synthetic peptide

<400> SEQUENCE: 32

Gln Gly Ile Ser His Tyr
1               5


<210> SEQ ID NO 33
<211> LENGTH: 3
<212> TYPE: PRT
<213> ORGANISM: Artificial sequence
<220> FEATURE:
<223> OTHER INFORMATION: Synthetic peptide

<400> SEQUENCE: 33

Ala Ala Ser
1


<210> SEQ ID NO 34
<211> LENGTH: 11
<212> TYPE: PRT
<213> ORGANISM: Artificial sequence
```

<220> FEATURE:
<223> OTHER INFORMATION: Synthetic peptide

<400> SEQUENCE: 34

Cys Gln Lys Tyr Asn Gly Ala Pro Phe Thr Phe
1 5 10

<210> SEQ ID NO 35
<211> LENGTH: 6
<212> TYPE: PRT
<213> ORGANISM: Artificial sequence
<220> FEATURE:
<223> OTHER INFORMATION: Synthetic peptide

<400> SEQUENCE: 35

Thr Leu Arg Ser Asn Tyr
1 5

<210> SEQ ID NO 36
<211> LENGTH: 3
<212> TYPE: PRT
<213> ORGANISM: Artificial sequence
<220> FEATURE:
<223> OTHER INFORMATION: Synthetic peptide

<400> SEQUENCE: 36

Gly Lys Asn
1

<210> SEQ ID NO 37
<211> LENGTH: 13
<212> TYPE: PRT
<213> ORGANISM: Artificial sequence
<220> FEATURE:
<223> OTHER INFORMATION: Synthetic peptide

<400> SEQUENCE: 37

Cys Asn Ser Arg Asp Ser Ser Gly Asn His Val Val Phe
1 5 10

<210> SEQ ID NO 38
<211> LENGTH: 6
<212> TYPE: PRT
<213> ORGANISM: Artificial sequence
<220> FEATURE:
<223> OTHER INFORMATION: Synthetic peptide

<400> SEQUENCE: 38

Gln Ser Ile Ser Arg Tyr
1 5

<210> SEQ ID NO 39
<211> LENGTH: 3
<212> TYPE: PRT
<213> ORGANISM: Artificial sequence
<220> FEATURE:
<223> OTHER INFORMATION: Synthetic peptide

<400> SEQUENCE: 39

Ala Ala Ser
1

<210> SEQ ID NO 40
<211> LENGTH: 11
<212> TYPE: PRT
<213> ORGANISM: Artificial sequence
<220> FEATURE:

-continued

```
<223> OTHER INFORMATION: Synthetic peptide

<400> SEQUENCE: 40

Cys Gln Glu Ser Ser Asn Thr Pro Pro Thr Phe
1               5                   10


<210> SEQ ID NO 41
<211> LENGTH: 21
<212> TYPE: DNA
<213> ORGANISM: Artificial sequence
<220> FEATURE:
<223> OTHER INFORMATION: Synthetic phosphorothioate-modified
      oligodeoxynucleotide
<220> FEATURE:
<221> NAME/KEY: modified_base
<222> LOCATION: (1)..(20)
<223> OTHER INFORMATION: phosphorothioate base

<400> SEQUENCE: 41

tcgtcgtttt tcggtcgttt t                                              21
```